US010239884B2

United States Patent
Suzuki et al.

(10) Patent No.: US 10,239,884 B2
(45) Date of Patent: Mar. 26, 2019

(54) COELENTERAZINE COMPOUNDS AND USES THEREOF

(71) Applicants: KEIO UNIVERSITY, Tokyo (JP); NATIONAL INSTITUTE OF ADVANCED INDUSTRIAL SCIENCE AND TECHNOLOGY, Tokyo (JP); The University of Tokyo, Tokyo (JP)

(72) Inventors: Koji Suzuki, Yokohama (JP); Daniel Citterio, Yokohama (JP); Ryo Nishihara, Yokohama (JP); Sung-Bae Kim, Tsukuba (JP); Moritoshi Sato, Tokyo (JP); Takahiro Nakajima, Tokyo (JP)

(73) Assignees: KEIO UNIVERSITY, Tokyo (JP); NATIONAL INSTITUTE OF ADVANCED INDUSTRIAL SCIENCE AND TECHNOLOGY, Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 15/926,204

(22) Filed: Mar. 20, 2018

(65) Prior Publication Data
US 2018/0273539 A1 Sep. 27, 2018

(30) Foreign Application Priority Data
Mar. 22, 2017 (JP) .................................. 2017-055985

(51) Int. Cl.
| | | |
|---|---|---|
| C07D 235/02 | (2006.01) | |
| C07D 487/04 | (2006.01) | |
| C07D 405/06 | (2006.01) | |
| C12Q 1/66 | (2006.01) | |
| C09K 11/06 | (2006.01) | |

(52) U.S. Cl.
CPC ......... *C07D 487/04* (2013.01); *C07D 405/06* (2013.01); *C09K 11/06* (2013.01); *C12Q 1/66* (2013.01); *C09K 2211/1022* (2013.01)

(58) Field of Classification Search
CPC ............................ C07D 235/02; C07D 487/04
See application file for complete search history.

(56) References Cited

PUBLICATIONS

Gales et al., "Real-time monitoring of receptor and G-protein interactions in living cells," Nat. Methods (Mar. 2005), vol. 2, No. 3, pp. 177-184 Epub Feb. 17, 2005.
Hart et al., "*Renilla reniformis* Bioluminescence: Luciferase-Catalyzed Production of Nonradiating Excited States from Luciferin Analogues and Elucidation of the Excited State Species Involved in Energy Transfer to *Renilla* Green Fluorescent Protein," Biochem. (1979), vol. 18, pp. 2204-2210.
Huang et al., "Bioluminescence measurements in mice using a skin window," J. Biomed. Opt. (Sep.-Oct. 2007), vol. 12, No. 5:054012.
Levi et al., "Bisdeoxycoelenterazine Derivatives for Improvement of Bioluminescence Resonance Energy Transfer Assays," J. Am. Chem. Soc. (Oct. 3, 2007), vol. 129, No. 39, pp. 11900-11901.
Pfleger et al., "Bioluminescence resonance energy transfer (BRET) for the real-time detection of protein-protein interactions," Nat. Protoc. (2006), vol. 1, No. 1, pp. 337-345.

*Primary Examiner* — Bruck Kifle
(74) *Attorney, Agent, or Firm* — Birch, Stewart, Kolasch & Birch, LLP

(57) ABSTRACT

There is provided a series of coelenterazine (CTZ) derivatives as a substrate with high luminescence intensity, which is optimal for maximum luminescence wavelengths at both 400 nm (blue-shifted RLuc luminescence system) and 500 nm (ALuc luminescence system) for bioassays which is more sensitive than known techniques. The novel CTZ derivatives are compounds in which a specific position(s) of the CTZ is/are substituted with a specific substituent(s) as shown, for example, by the Formula [I],

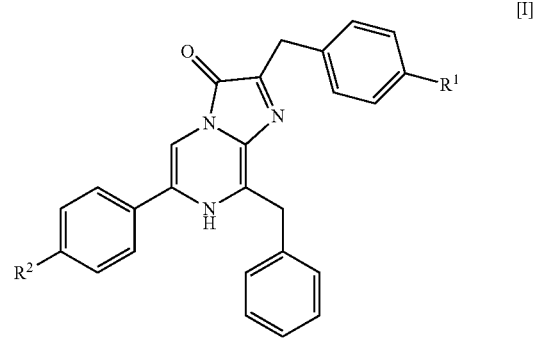

[I]

and has a higher luminescence intensity than known CTZ derivatives in blue-shifted RLuc luminescence system or ALuc luminescence system.

6 Claims, 2 Drawing Sheets
(2 of 2 Drawing Sheet(s) Filed in Color)

COELENTERAZINE COMPOUNDS AND USES THEREOF

BACKGROUND OF THE INVENTION

Field of the Invention

The present invention relates to novel coelenterazine compounds and uses thereof as luminescent substrates for luciferases.

Description of the Related Art

Bioassays using bioluminescence are highly sensitive and thus are very useful in life science studies such as gene expression profiling with microanalysis and bioimaging. Since bioluminescence produces light via an enzymatic reaction involving a luminescent substrate and luciferase, it is not affected by background signals derived from excitation light in fluorescence measurements, and its quantum yield is said to be higher than chemiluminescence quantum yields. The firefly luminescence system is most widely applied to bioassays utilizing bioluminescence. However, the firefly luminescence system requires complicated experimental procedures because it needs cofactors such as ATP and Mg ions in the luminescence process. In particular, the concentration of Mg ions in a cell fluctuates unpredictably, and thus reliable and reproducible data are not necessarily obtained by bioanalysis using the firefly luminescence system. On the other hand, the *Renilla* Luciferase (RLuc) luminescence system using coelenterazine (CTZ) as a luminescent substrate, which is a simple luminescence system that does not require any cofactor other than molecular oxygen, enables reproducible analysis not only in cells but also outside cells where ATP is absent. Although the RLuc luminescence system has been applied to, for example, dual luciferase assay combined with the firefly luminescence system and protein interaction assays, the quantum yield of the RLuc luminescence system is 0.05, which is very low compared to the firefly luminescence system. Therefore, if a high-intensity bioluminescence system with CTZ as a luminescent substrate is constructed, it will be increasingly used in the future as a more sensitive bioassay tool.

In order to construct the high-intensity bioluminescence system, the enzyme (luciferase) or the substrate (luciferin) has been modified. Studies on improvements of bioluminescence intensity by enzyme modification have been reported. For example, Loening et al. (2006) have reported RLuc8 as a high-intensity luminescent enzyme, wherein 8 amino acid residues in RLuc were modified, which has not only improved stability in mouse serum but also greatly improved enzyme activity with the substrate coelenterazine and its derivatives. ALuc (Artificial Luciferase), an artificial luciferase developed in recent years, provides a luminescence system with CTZ as a luminescent substrate like the RLuc luminescence system. ALuc has an extremely high luminescence intensity of about 50 fold higher than that of the RLuc luminescence system and has excellent luminescence sustainability (half life: 20 minutes) in lysates. On the other hand, there have been few examples and few findings on improvement in the luminescence intensity by a substrate modification.

PRIOR ART REFERENCES

Non-Patent Documents

Non-Patent Document 1: Hart, C. R., et al., Biochem., 1979, 18, 2204-2210.
Non-Patent Document 2: Levi, J., et al., J. Am. Chem. Soc., 2007, 129, 11900-11901.
Non-Patent Document 3: Pfleger, K. D. G., et al., Nat. Protocols, 2006, 1, 337-345.
Non-Patent Document 4: Galés, C., et al., Nat. Methods, 2005, 2, 177-184.
Non-Patent Document 5: Huang, Q. et al., J. Biomed. Opt., 2007, 12, 1-10.

SUMMARY OF THE INVENTION

Various researches have been actively conducted to develop CTZ derivatives, where the luminescence wavelength and intensity of CTZs were changed by chemical modifications while maintaining the skeleton of CTZ which acts as the luminescent substrate. Among these derivatives, a blue-shifted derivative DeepBlueC (trade name) (Non-Patent Document 1) has been applied to, for example, protein-protein interaction analyses by combining it with GFP, since DeepBlueC emits light at around 400 nm, where the luminescence wavelength has been shifted to the shorter wavelength side by about 80 nm compared to native CTZ. It is beneficial because the blue shift of the luminescence wavelength still overlaps with the excitation spectrum of green fluorescent protein (GFP) and does not mix up with the emission of GFP. Thus, the optical characteristics specific to CTZ derivatives play an important role in expanding the range of use of CTZ as a bioanalytical tool. However, DeepBlueC (trade name) has a remarkably decreased luminescence intensity due to its functional group modification, which is about 4% of the native RLuc luminescence system. Therefore, in order to accomplish highly sensitive bioassays based on the coelenterazine luminescence system, development of novel CTZ derivatives is greatly beneficial. However, detailed enzyme recognition mechanisms between RLuc or its derivatives and CTZ are unknown, and thus it is difficult to design CTZ analogues that show strong bioluminescence. Although a bioluminescence system generating high-intensity luminescence at around 500 nm has already been achieved by the development of ALuc, native CTZ is not necessarily the optimal substrate for ALuc.

An object of the present invention is to develop CTZ derivatives with high luminescence intensity, which are optimal for maximum luminescence wavelengths of 400 nm (blue-shifted RLuc luminescence system) and 500 nm (ALuc luminescence system) for accomplishing sensitive bioassays.

The present inventors have intensively studied to find novel CTZ derivatives that have a higher luminescence intensity than known CTZ derivatives for blue-shifted RLuc luminescence system or ALuc luminescence system by replacing a specific position(s) of CTZ with a specific substituent(s), thereby completing the present invention.

Accordingly, the present invention provides a compound represented by the General Formula [II]:

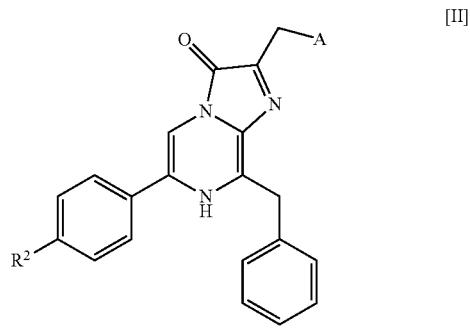

wherein
A represents

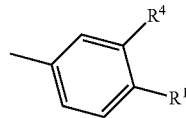

wherein,
R¹ represents hydrogen, hydroxy or fluorine; and
R⁴ represents hydrogen, methyl or methoxy;
or
A represents

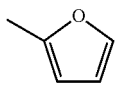

R² represents
(1) —O—$(CH_2)_n$—R³, where n is an integer from 1 to 5; and R³ represents hydroxy, methoxy, methyl or azido; or
(2) $C_1$- or $C_2$-alkyl.

The present invention also provides a method of generating luminescence, comprising contacting the above-mentioned compound of the present invention with a luciferase.

The compound of the present invention has a higher luminescence intensity than known CTZ derivatives in blue-shifted RLuc luminescence system or ALuc luminescence system. Therefore, use of the compound of the present invention as a luminescent substrate for luciferases enables analyses with higher sensitivity and higher accuracy than before.

BRIEF DESCRIPTION OF THE DRAWINGS

The patent or application file contains at least one color drawing. Copies of this patent or patent application publication with color drawing will be provided by the USPTO upon request and payment of the necessary fee.

DETAILED DESCRIPTION OF PREFERRED EMBODIMENTS

Figure 1:
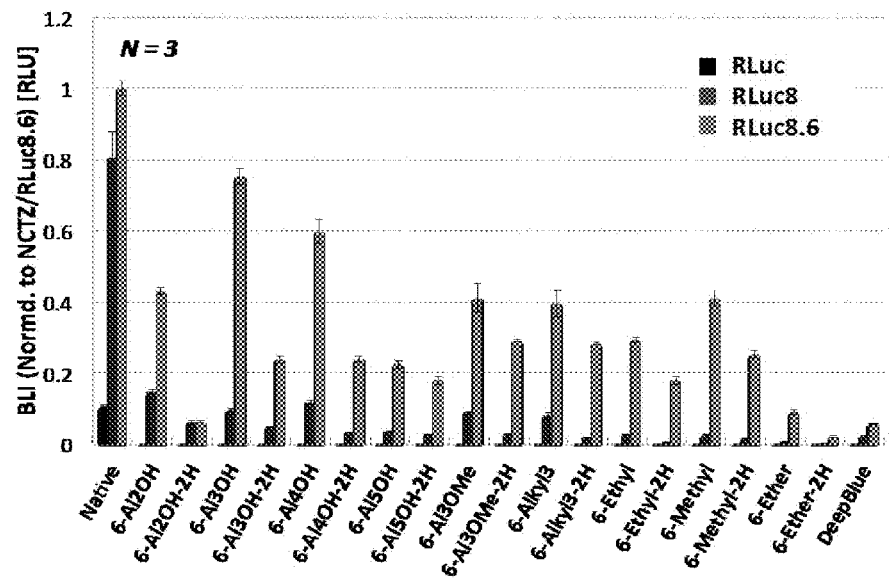
FIG. 1 shows the luminescence intensity of each of the compounds obtained in Examples and Comparative Examples of the present invention in a luciferase luminescence system.
Figure 2:
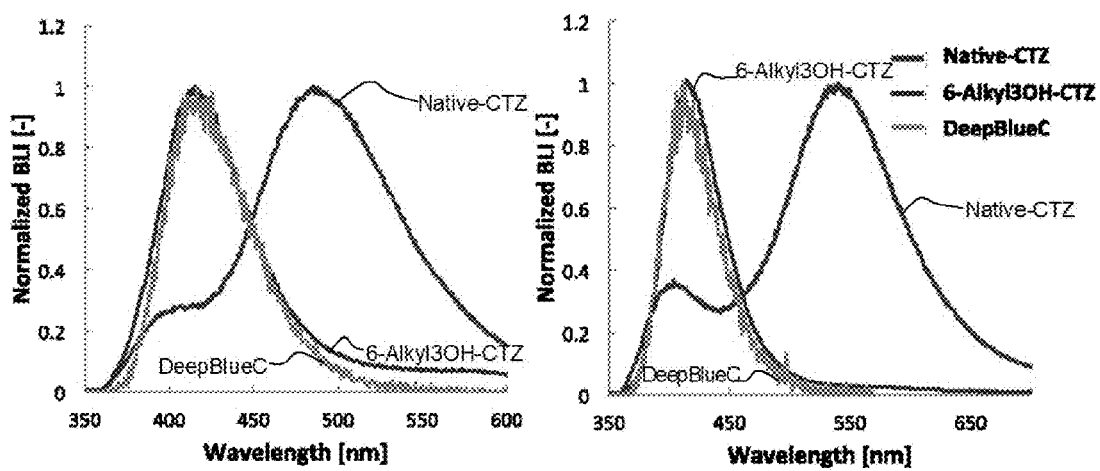
FIG. 2 shows the luminescence wavelength of each of the compounds obtained in Examples and Comparative Examples of the present invention with RLuc8 (left) or RLuc8.6 (right).

As described above, the compound of the present invention is represented by the General Formula [II] above. Among the compounds represented by the above General Formula [II], preferred are compounds represented by the following General Formula [I]:

General Formula [I]

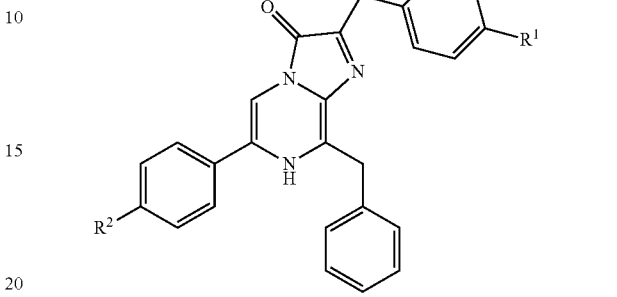

wherein,
R¹ represents hydrogen or hydroxy; and
R² represents
(1) —O—$(CH_2)_n$—R³, where n is an integer from 2 to 5; and R³ represents hydroxy, methoxy, methyl or azido; or
(2) $C_1$- or $C_2$-alkyl.

In the General Formula [I], preferred examples of the combination of R¹ and R² include those listed in Table 1 below.

TABLE 1

| Compound name | R¹ | R² |
|---|---|---|
| 6-Al2OH-CTZ | —OH | —O—$(CH_2)_2$—OH |
| 6-Al3OH-CTZ | —OH | —O—$(CH_2)_3$—OH |
| 6-Al4OH-CTZ | —OH | —O—$(CH_2)_4$—OH |
| 6-Al5OH-CTZ | —OH | —O—$(CH_2)_5$—OH |
| 6-Al3OMe-CTZ | —OH | —O—$(CH_2)_3$—OCH₃ |
| 6-Al2N3-CTZ | —OH | —O—$(CH_2)_2$—N₃ |
| 6-Alkyl3-CTZ | —OH | —O—$(CH_2)_3$—CH₃ |
| 6-Al2OH-2H-CTZ | —H | —O—$(CH_2)_2$—OH |
| 6-Al3OH-2H-CTZ | —H | —O—$(CH_2)_3$—OH |
| 6-Al4OH-2H-CTZ | —H | —O—$(CH_2)_4$—OH |
| 6-Al5OH-2H-CTZ | —H | —O—$(CH_2)_5$—OH |
| 6-Al3OMe-2H-CTZ | —H | —O—$(CH_2)_3$—OCH₃ |
| 6-Alkyl3-2H-CTZ | —H | —O—$(CH_2)_3$—CH₃ |
| 6-Ethyl-CTZ | —OH | —$C_2H_5$ |
| 6-Ethyl-2H-CTZ | —H | —$C_2H_5$ |
| 6-Methyl-CTZ | —OH | —CH₃ |
| 6-Methyl-2H-CTZ | —H | —CH₃ |

It is noted that R¹ and R² are both —OH in the known CTZ (native CTZ (sometimes referred to as "nCTZ")) while they are both —H in the known DeepBlueC (trade name).

As shown in the following reaction scheme, the compounds of the present invention can be prepared, for example, by condensing a ketoacetal compound (wherein $R^{1a}$ represents hydroxyl protected with TBS (t-butyldimethylsilyl) or hydrogen) and a coelenteramine derivative (wherein R² is as defined above; the same shall apply hereinafter).

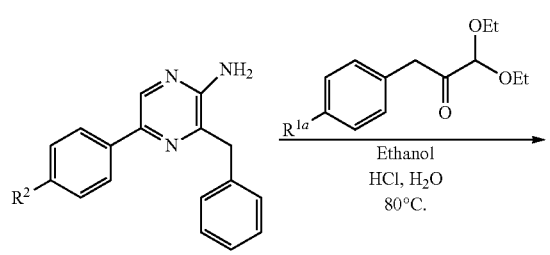
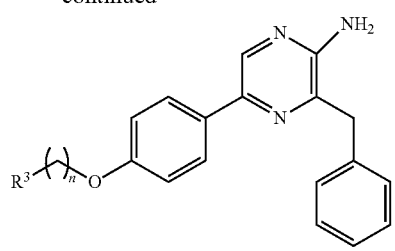

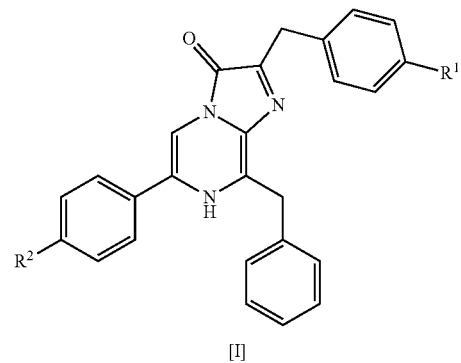

[I]

The coelenteramine derivatives used as a starting material in the above reaction scheme and used in the preparation of the compounds in which R² in the General Formula [I] is —O—(CH$_2$)$_n$—R³ can be prepared, for example, according to the following reaction scheme. In all the following reaction schemes, "Boronic acid" means a boronic acid derivative shown in each reaction scheme.

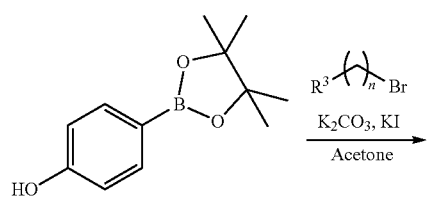

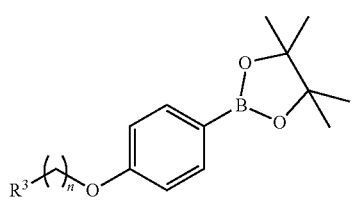

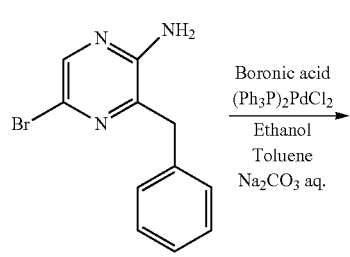

Further, the coelenteramine derivatives used as a starting material in the above reaction scheme and used in the preparation of the compounds in which R² in the General Formula [I] is C$_1$- or C$_2$-alkyl can be prepared, for example, according to the following reaction scheme.

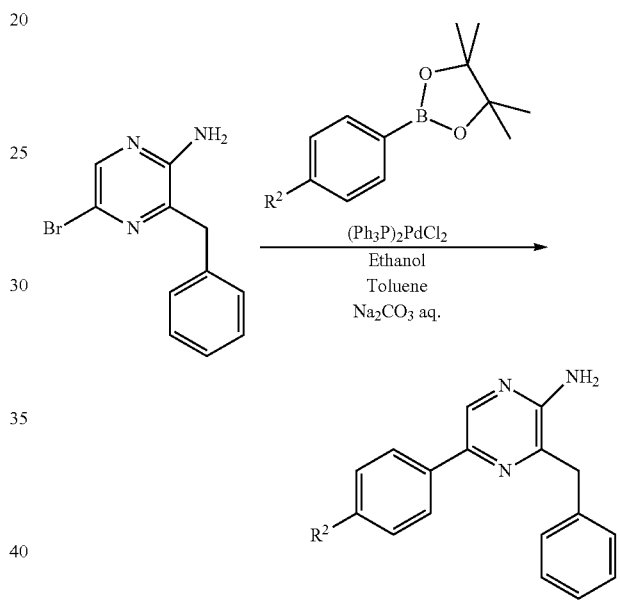

The specific conditions of each step in each of the above schemes can be appropriately set by a person skilled in the art and are also described in detail in the following Synthesis Examples.

The compound of the present invention can be used as a luminescent substrate for luciferases as described in detail in the following Examples. Examples of the luciferases include RLuc8 (see Loening, A. M. et al., Protein Eng. Des. Sel. 2006, 19, 391-400, Loening, A. M. et al., J. Mol. Biol. 2007, 374, 1017-1028., Loening, A. M. et al., Protein Eng. Des. Sel. 2006, 19, 391-400.) and RLuc8.6 (see Loening, A. M. et al., Nat. Methods, 2007, 4, 641-643.) in *Renilla* Luciferase (RLuc) luminescence system, as well as ALuc group such as ALuc16, ALuc22, ALuc23, ALuc24, ALuc30, ALuc34 in ALuc luminescence system (see Kim S. B. et al., Bioconjugate Chem., 2013, 24, 2067-2075., Kim S. B. et al., Biochem. Biophys. Res. Commun., 2014, 448, 418-423., Kim S. B. et al., Anal. Sci., 2015, 31, 1-6., Kim S. B. et al., Bioconjugate Chem., 27, 354-362.).

The present invention will now be described in detail with reference to Examples. However, the present invention is not limited to these Examples.

EXAMPLES

Synthesis Method

Reagents were purchased from Wako Pure Chemical Industries, Kanto Chemical, Tokyo Chemical, or Sigma-Aldrich, and used without further purification. In the synthesis of CTZ derivatives, silica gel (Merck, 1.07734.9025, silica gel 60 (0.063-0.200 mm) for column chromatography (70-230 mesh ASTM)) was used for silica column chromatography. YFLC-Al-560 chromatograph produced by Yamazen Corporation was used for flash column chromatography. High performance liquid chromatography (HPLC) was performed using LC-918 recycling preparative HPLC produced by Japan Analytical Industry Co., Ltd. and Inertsil ODS-3 analytical column (C18, 5 μm, 20×250 mm) produced by GL Sciences. $^1$H- and $^{13}$C-NMR were measured on a JEOL ECA500 using tetramethylsilane (TMS, 0 ppm) as an internal standard. Coupling constant (J) were shown in Hz. Abbreviations s, d, t, q, m and br refer to singlet, doublet, triplet, quartet, multiplet and broad signal, respectively.

Synthesis Example 1: Synthesis of 6-Al2OH-CTZ

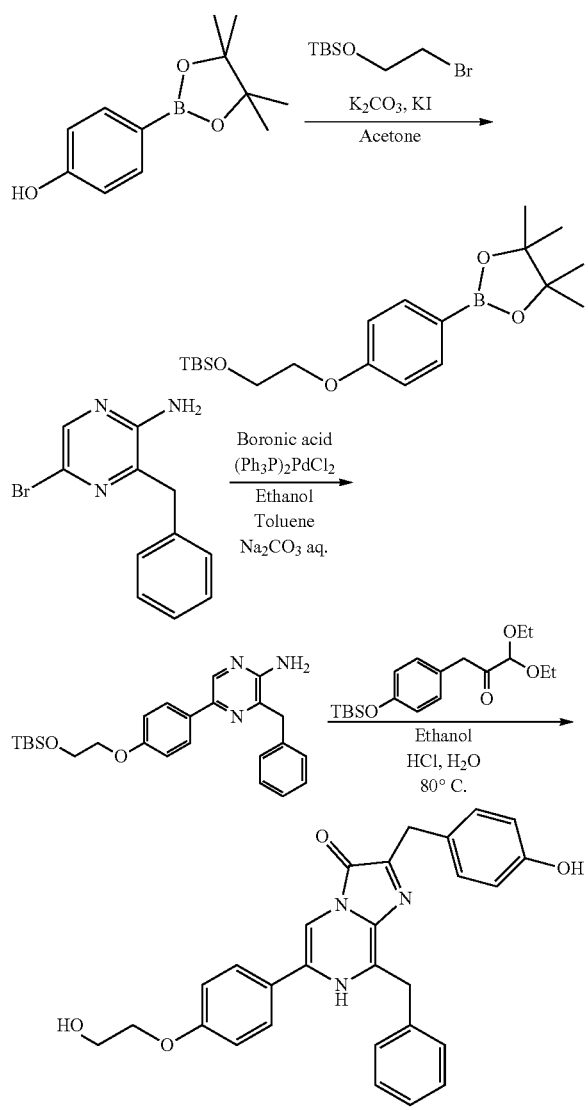

Synthesis Example 1-1

Under a nitrogen atmosphere, 4-(4,4,5,5-tetramethyl-1,3,2-dioxaborolan-2-yl)phenol (500.0 mg, 2.2 mmol, 1 eq.) and potassium carbonate (410 mg, 2.9 mmol, 1.3 eq.) were dissolved in acetone (20 ml) and the solution was stirred at room temperature. To the stirred solution were added (2-bromoethoxy(tert-butyl)dimethylsilane (812.0 mg, 3.4 mmol, 1.5 eq.) and potassium iodide (20 mg, 0.1 mmol, 0.05 eq.) dissolved in acetone (20 ml), and the mixture was stirred at 70° C. for 24 hours. After allowing the mixture to cool to room temperature, the mixture was concentrated under reduced pressure. The obtained residue was extracted with ethyl acetate, washed with distilled water and saturated brine, dried over sodium sulfate, and then concentrated again under reduced pressure. The resulting residue was purified by flash column chromatography (eluent: hexane/ethyl acetate=8/2), to obtain tert-butyldimethyl (2-(4-(4,4,5,5-tetramethyl-1,3,2-dioxaborolan-2-yl)phenoxy)ethoxy)silane as a white solid (307.0 mg, 36%).

$^1$H-NMR (500 MHz, CD$_3$OD): δ (ppm)=7.73 (d, J=8.5 Hz, 2H), 6.89 (d, J=8.5 Hz, 2H), 4.05 (t, J=5.1 Hz, 2H), 3.97 (t, J=5.4 Hz, 2H), 1.33 (m, 12H), 0.90 (s, 9H), 0.09 (s, 6H). $^{13}$C-NMR (150 MHz, CDCl$_3$): δ (ppm)=−5.05, 18.54, 24.99, 26.05, 62.07, 69.18, 83.66, 114.02, 136.61, 161.64. HR-MS: m/z calcd for C$_{20}$H$_{35}$BO$_4$Si: 379.2476, found: 379.2477 [M+H]$^+$.

Synthesis Example 1-2

Under a nitrogen atmosphere, 3-benzyl-5-bromopyrazine-2-amine (150.0 mg, 0.56 mmol, 1 eq.) and tert-butyldimethyl (2-(4-(4,4,5,5-tetramethyl-1,3,2-dioxaborolan-2-yl)phenoxy)ethoxy)silane (307.0 mg, 0.8 mmol, 1.4 eq.) were dissolved in ethanol (2 ml) and toluene (12 ml). To the solution was added 1 M aqueous sodium carbonate solution (3 ml) and the mixture was stirred at room temperature. The reaction solution was degassed under vacuum. To the solution was added a catalytic amount of tetrakis(triphenylphosphine)palladium (0) (about 1 cup of micro spatula) and the mixture was degassed again under vacuum and then stirred at 100° C. overnight (12 hours). After allowing the mixture to cool to room temperature, the mixture was filtered through Celite to remove palladium catalyst. The resulting residue was extracted with ethyl acetate, washed with distilled water and saturated brine, dried over sodium sulfate, and then concentrated under reduced pressure. The resulting residue was purified by flash column chromatography (eluent: hexane/ethyl acetate=8/2→7/3) to obtain 3-benzyl-5-(4-(2-((tert-butyldimethylsilyl)oxy)ethoxy)phenyl)pyrazine-2-amine as a yellow solid (225.0 mg, 92%).

$^1$H-NMR (500 MHz, CDCl$_3$): δ (ppm)=8.33 (s, 1H), 7.86 (d, J=8.5 Hz, 2H), 7.33-7.24 (m, 5H), 6.99 (d, J=8.5 Hz, 2H), 4.33 (s, 2H), 4.17 (s, 2H), 4.09 (t, J=5.1 Hz, 2H), 4.00 (t, J=5.1 Hz, 2H), 0.92 (s, 12H), 0.11 (s, 6H). $^{13}$C-NMR (125 MHz, CDCl$_3$): δ (ppm)=−5.02, 18.56, 26.07, 41.40, 62.13, 69.52, 115.00, 127.11, 127.15, 128.70, 129.10, 130.14, 136.99, 140.58, 142.77, 151.38, 159.26. HR-MS: m/z calcd for C$_{25}$H$_{33}$N$_3$O$_2$Si: 436.2420, found: 436.2426 [M+H]$^+$.

Synthesis Example 1-3

Under an argon atmosphere, 3-benzyl-5-(4-(2-((tert-butyldimethylsilyl)oxy)ethoxy)phenyl)pyrazine-2-amine (30.0 mg, 0.06 mmol, 1 eq.) and 3-(4-((tert-butyldimethylsilyl)oxy)phenyl)-1,1-diethoxypropan-2-one (47.9 mg, 0.13 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 5 hours. After allowing the mixture to cool to room temperature, the mixture was concentrated under reduced pressure, and the residue was purified by chromatography using reversed-phase HPLC columns (eluent: methanol/water=6/4+0.1% formic acid) to obtain 6-Al2OH-CTZ as a yellow solid (12.8 mg, 45%).

$^1$H-NMR (500 MHz, CD$_3$OD): δ (ppm)=7.63 (s, 1H), 7.56 (d, J=8.3 Hz, 2H), 7.39-7.21 (m, 5H), 7.15 (d, J=8.3 Hz, 2H), 7.03 (d, J=8.3 Hz, 2H), 6.69 (d, J=8.5 Hz, 2H), 4.39 (s, 2H), 4.08-4.06 (m, 4H), 3.88 (t, J=4.8 Hz, 2H). $^{13}$C-NMR (150 MHz, CD$_3$OD, CDCl$_3$): δ (ppm)=33.20, 61.60, 70.74, 108.17, 116.07, 116.19, 128.13, 129.30, 129.74, 129.78, 130.78, 138.16, 156.97, 161.57. HR-MS: m/z calcd for C$_{28}$H$_{25}$N$_3$O$_4$: 468.1923, found: 468.1923 [M+H]$^+$.

Synthesis Example 2: Synthesis of 6-Al3OH-CTZ

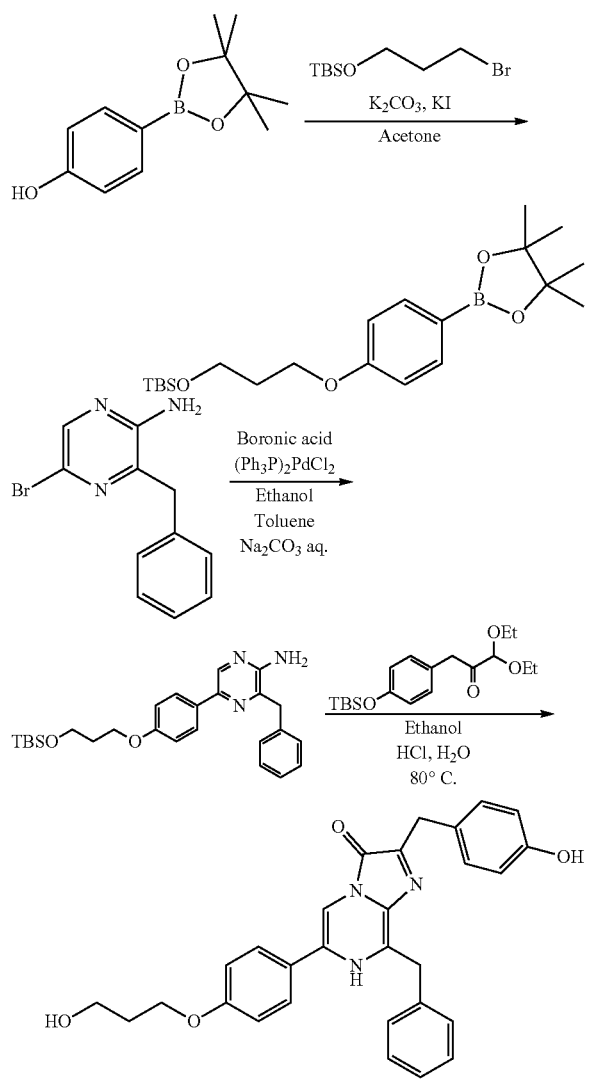

Synthesis Example 2-1

Under a nitrogen atmosphere, 4-(4,4,5,5-tetramethyl-1,3,2-dioxaborolan-2-yl)phenol (500.0 mg, 2.2 mmol, 1 eq.) and potassium carbonate (410 mg, 2.9 mmol, 1.3 eq.) were dissolved in acetone (20 ml) and the solution was stirred at room temperature. To the stirred solution were added (3-bromopropoxy)(tert-butyl)dimethylsilane (690.0 mg, 2.7 mmol, 1.2 eq.) and potassium iodide (20 mg, 0.1 mmol, 0.05 eq.) dissolved in acetone (20 ml), and the mixture was stirred at 70° C. for 13 hours. After allowing the mixture to cool to room temperature, the mixture was concentrated under reduced pressure. The resulting residue was extracted with ethyl acetate, washed with distilled water and saturated brine, dried over sodium sulfate, and then concentrated again under reduced pressure. The resulting residue was purified by flash column chromatography (eluent: hexane/ethyl acetate=8/2), to obtain tert-butyldimethyl (3-(4-(4,4,5,5-tetramethyl-1,3,2-dioxaborolan-2-yl)phenoxy)propoxy)silane as a white solid (489.3 mg, 63%).

$^1$H-NMR (500 MHz, CD$_3$OD): δ (ppm)=7.73 (d, J=8.5 Hz, 2H), 6.89 (d, J=8.5 Hz, 2H), 4.08 (t, J=6.3 Hz, 2H), 3.79 (t, J=6.3 Hz, 2H), 1.97 (m, 2H), 1.32 (s, 12H), 0.88 (s, 9H), 0.03 (s, 6H). $^{13}$C-NMR (150 MHz, CDCl$_3$): δ (ppm)=−5.24, 18.45, 25.00, 26.05, 32.45, 59.57, 64.33, 83.67, 113.97, 136.60, 161.79. HR-MS: m/z calcd for C$_{21}$H$_{37}$BO$_4$Si: 393.2632, found: 393.2609 [M+H]$^+$.

Synthesis Example 2-2

Under a nitrogen atmosphere, 3-benzyl-5-bromopyrazine-2-amine (308.0 mg, 1.16 mmol, 1 eq.) and tert-butyldimethyl (3-(4-(4,4,5,5-tetramethyl-1,3,2-dioxaborolan-2-yl)phenoxy)propoxy)silane (702.29 mg, 1.85 mmol, 1.6 eq.) were dissolved in ethanol (2 ml) and toluene (12 ml). To the solution was added 1 M aqueous sodium carbonate solution (3 ml) and the mixture was stirred at room temperature. The reaction solution was degassed under vacuum. To the solution was added a catalytic amount of tetrakis(triphenylphosphine)palladium (0) (about 1 cup of micro spatula) and the mixture was degassed again under vacuum and then stirred at 100° C. overnight (18 hours). After allowing the mixture to cool to room temperature, the mixture was filtered through Celite to remove palladium catalyst. The resulting residue was extracted with ethyl acetate, washed with distilled water and saturated brine, dried over sodium sulfate, and then concentrated under reduced pressure. The resulting residue was purified by flash column chromatography (eluent: hexane/ethyl acetate=8/2→7/3) to obtain 3-benzyl-5-(4-(3-((tert-butyldimethylsilyl)oxy)propoxy)phenyl)pyrazine-2-amine as a yellow solid (478.9 mg, 91%).

$^1$H-NMR (500 MHz, CDCl$_3$): δ (ppm)=8.33 (s, 1H), 7.86 (d, J=8.5 Hz, 2H), 7.33-7.25 (m, 5H), 6.98 (d, J=8.5 Hz, 2H), 4.34 (s, 2H), 4.17 (s, 2H), 4.11 (t, J=6.3 Hz, 2H), 3.82 (t, J=5.7 Hz, 2H), 2.00 (quin, J=6.0 Hz, 2H), 0.89 (s, 12H), 0.05 (s, 6H). $^{13}$C-NMR (125 MHz, CDCl$_3$): δ (ppm)=−5.21, 18.47, 26.07, 32.50, 41.42, 59.60, 64.67, 114.93, 127.11, 127.15, 128.71, 129.10, 129.93, 137.00, 140.58, 142.86, 151.34, 159.40. HR-MS: m/z calcd for C$_{26}$H$_{35}$N$_3$O$_2$Si: 450.2577, found: 450.2557 [M+H]$^+$.

Synthesis Example 2-3

Under an argon atmosphere, 3-benzyl-5-(4-(3-((tert-butyldimethylsilyl)oxy)propoxy)phenyl)pyrazine-2-amine (30.0 mg, 0.06 mmol, 1 eq.) and 3-(4-((tert-butyldimethylsilyl)oxy)phenyl)-1,1-diethoxypropan-2-one (48.2 mg, 0.13 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 5.5 hours. After allowing the mixture to cool to room temperature, the mixture was concentrated under reduced pressure, and the residue was purified by chromatography using reversed-phase HPLC columns (eluent: methanol/water=6/4+0.1% formic acid) to obtain 6-Al3OH-CTZ as a yellow solid (6.55 mg, 20%).

$^1$H-NMR (500 MHz, CD$_3$OD): δ (ppm)=7.61 (s, 1H), 7.54 (d, J=8.0 Hz, 2H), 7.38-7.20 (m, 5H), 7.14 (d, J=8.5 Hz, 2H), 7.00 (d, J=8.8 Hz, 2H), 6.69 (d, J=8.5 Hz, 2H), 4.39 (s, 2H), 4.10 (t, J=6.3 Hz, 2H), 4.06 (s, 2H), 3.73 (t, J=6.3 Hz, 2H), 1.98 (q, J=6.3 Hz, 2H). $^{13}$C-NMR (150 MHz, CD$_3$OD, CDCl$_3$): δ (ppm)=33.27, 59.44, 65.90, 108.10, 115.99, 116.20, 128.15, 129.27, 129.75, 130.67, 130.79, 138.13, 156.99, 161.65. HR-MS: m/z calcd for C$_{29}$H$_{27}$N$_3$O$_4$: 482.2080, found: 482.2051 [M+H]$^+$.

Synthesis Example 3: Synthesis of 6-Al4OH-CTZ mobutoxy)(tert-butyl)dimethylsilane (721.6 mg, 2.7 mmol, 1.2 eq.) and potassium iodide (20 mg, 0.1 mmol, 0.05 eq.) dissolved in acetone (20 ml), and the mixture was stirred at 70° C. for 13 hours. After allowing the mixture to cool to room temperature, the mixture was concentrated under reduced pressure. The resulting residue was extracted with ethyl acetate, washed with distilled water and saturated brine, dried over sodium sulfate, and then concentrated again under reduced pressure. The resulting residue was purified by flash column chromatography (eluent: hexane/ethyl acetate=8/2), to obtain tert-butyldimethyl (4-(4-(4,4,5,5-tetramethyl-1,3,2-dioxaborolan-2-yl)phenoxy)butoxy)silane as a white solid (881 mg, 95%).

$^1$H-NMR (500 MHz, CD$_3$OD): δ (ppm)=7.73 (d, J=7.4 Hz, 2H), 6.87 (d, J=7.4 Hz, 2H), 4.00 (t, J=6.0 Hz, 2H), 3.68-3.63 (m, 2H), 1.86-1.81 (m, 2H), 1.70-1.65 (m, 2H), 1.32 (s, 12H), 0.89 (s, 9H), 0.05 (s, 6H). $^{13}$C-NMR (150 MHz, CDCl$_3$): δ (ppm)=−5.16, 18.46, 24.98, 25.97, 26.09,

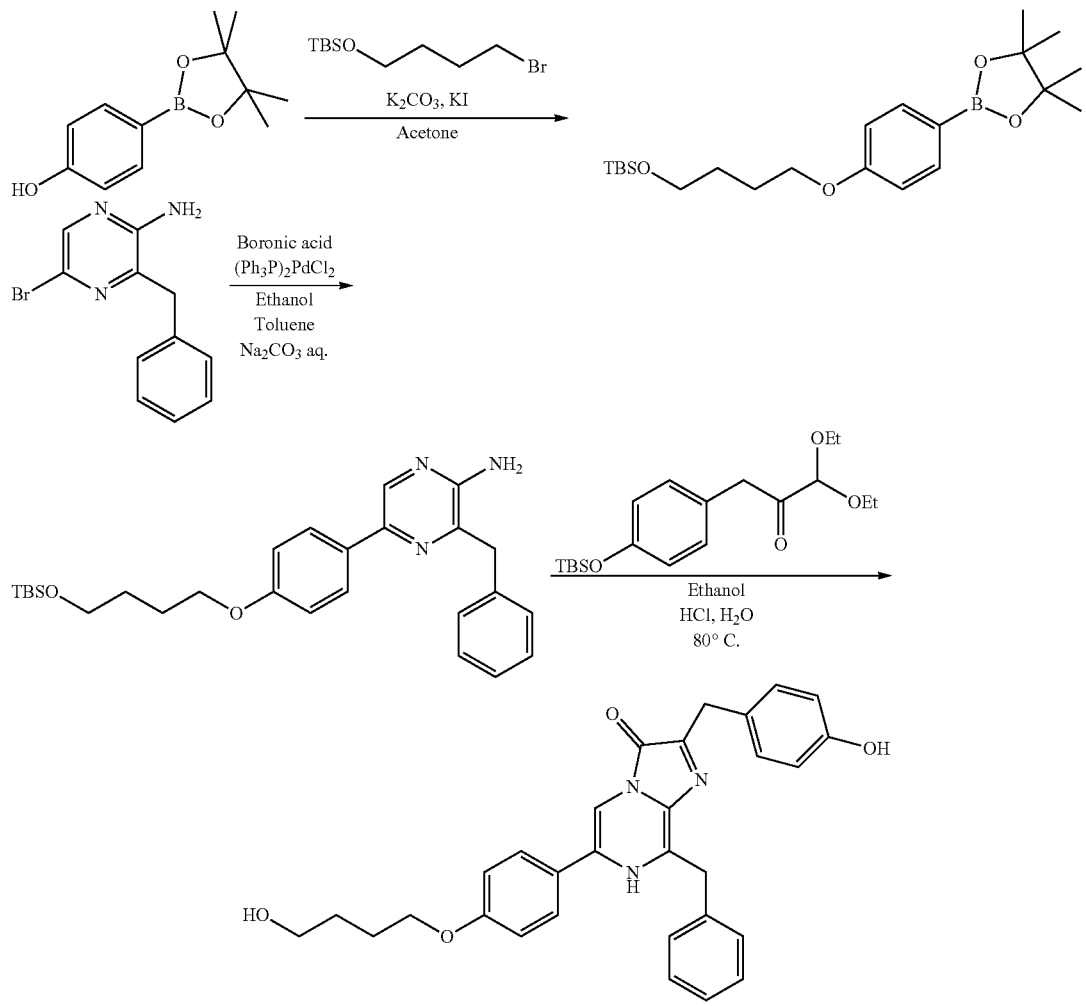

Synthesis Example 3-1

Under a nitrogen atmosphere, 4-(4,4,5,5-tetramethyl-1,3,2-dioxaborolan-2-yl)phenol (500.0 mg, 2.2 mmol, 1 eq.) and potassium carbonate (410 mg, 2.9 mmol, 1.3 eq.) were dissolved in acetone (20 ml) and the solution was stirred at room temperature. To the stirred solution were added (4-bro- 29.44, 62.91, 67.70, 83.63, 113.95, 136.60, 161.81. HR-MS: m/z calcd for C$_{22}$H$_{39}$BO$_4$Si: 407.2789, found: 407.2779 [M+H]$^+$.

Synthesis Example 3-2

Under a nitrogen atmosphere, 3-benzyl-5-bromopyrazine-2-amine (180.0 mg, 0.68 mmol, 1 eq.) and tert-butyldimethyl (4-(4-(4,4,5,5-tetramethyl-1,3,2-dioxaborolan-2-yl)phenoxy)butoxy)silane (443.0 mg, 1.09 mmol, 1.6 eq.) were dissolved in ethanol (2 ml) and toluene (10 ml). To the solution was added 1 M aqueous sodium carbonate solution (3 ml) and the mixture was stirred at room temperature. The reaction solution was degassed under vacuum. To the solution was added a catalytic amount of tetrakis(triphenylphosphine)palladium (0) (about 1 cup of micro spatula) and the mixture was degassed again under vacuum and then stirred at 100° C. overnight (15 hours). After allowing the mixture to cool to room temperature, the mixture was filtered through Celite to remove palladium catalyst. The resulting residue was extracted with ethyl acetate, washed with distilled water and saturated brine, dried over sodium sulfate, and then concentrated under reduced pressure. The resulting residue was purified by flash column chromatography (eluent: hexane/ethyl acetate=8/2→7/3) to obtain 3-benzyl-5-(4-(4-((tert-butyldimethylsilyl)oxy)butoxy)phenyl)pyrazine-2-amine as a yellow solid (303.5 mg, 96%).

$^1$H-NMR (500 MHz, CDCl$_3$): δ (ppm)=8.32 (s, 1H), 7.86 (d, J=8.8 Hz, 2H), 7.30-7.25 (m, 5H), 6.97 (d, J=8.5 Hz, 2H), 4.34 (s, 2H), 4.17 (s, 2H), 4.03 (t, J=6.5 Hz, 2H), 3.69 (t, J=6.3 Hz, 2H), 1.89-1.84 (m, 2H), 1.73-1.69 (m, 2H), 0.90 (s, 12H), 0.06 (s, 6H). $^{13}$C-NMR (125 MHz, CDCl$_3$): δ (ppm)=−5.13, 18.49, 26.02, 26.11, 29.48, 41.42, 62.95, 68.04, 114.94, 127.12, 127.16, 128.71, 129.11, 129.94, 136.99, 140.58, 142.87, 151.34, 159.42. HR-MS: m/z calcd for C$_{27}$H$_{37}$N$_3$O$_2$Si: 467.2733, found: 464.2724 [M+H]$^+$.

Synthesis Example 3-3

Under an argon atmosphere, 3-benzyl-5-(4-(4-((tert-butyldimethylsilyl)oxy)butoxy)phenyl)pyrazine-2-amine (30.0 mg, 0.06 mmol, 1 eq.) and 3-(4-((tert-butyldimethylsilyl)oxy)phenyl)-1,1-diethoxypropan-2-one (48.5 mg, 0.13 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 7 hours. After allowing the mixture to cool to room temperature, the mixture was concentrated under reduced pressure, and the residue was purified by chromatography using reversed-phase HPLC columns (eluent: acetonitrile/water=1/1+0.1% formic acid) to obtain 6-Al4OH-CTZ as a yellow solid (6.96 mg, 20%).

$^1$H-NMR (500 MHz, CD$_3$OD): δ (ppm)=7.61 (s, 1H), 7.54 (d, J=8.3 Hz, 2H), 7.38-7.21 (m, 5H), 7.14 (d, J=8.3 Hz, 2H), 6.98 (d, J=8.3 Hz, 2H), 6.68 (d, J=8.3 Hz, 2H), 4.39 (s, 2H), 4.06 (s, 2H), 4.02 (t, J=6.3 Hz, 2H), 3.62 (t, J=6.3 Hz, 2H), 1.86-1.82 (m, 2H), 1.73-1.69 (m, 2H). $^{13}$C-NMR (150 MHz, CD$_3$OD, CDCl$_3$): δ (ppm)=26.86, 30.17, 33.24, 35.21, 62.61, 69.00, 108.10, 115.97, 116.19, 128.13, 129.25, 129.74, 129.77, 130.71, 130.78, 138.16, 156.97, 161.65. HR-MS: m/z calcd for C$_{30}$H$_{29}$N$_3$O$_4$: 496.2236, found: 496.2214 [M+H]$^+$.

Synthesis Example 4: Synthesis of 6-Al5OH-CTZ

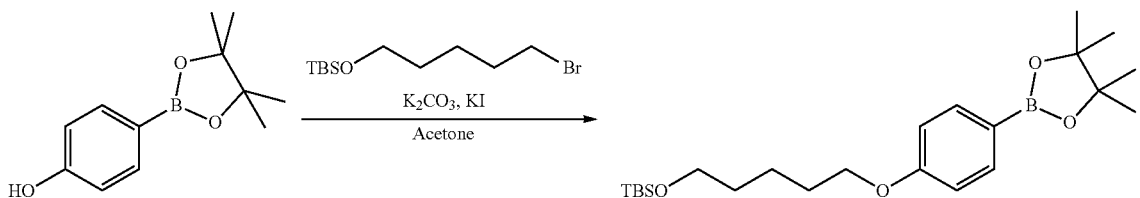

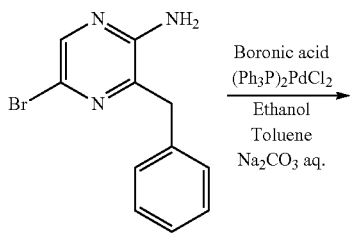

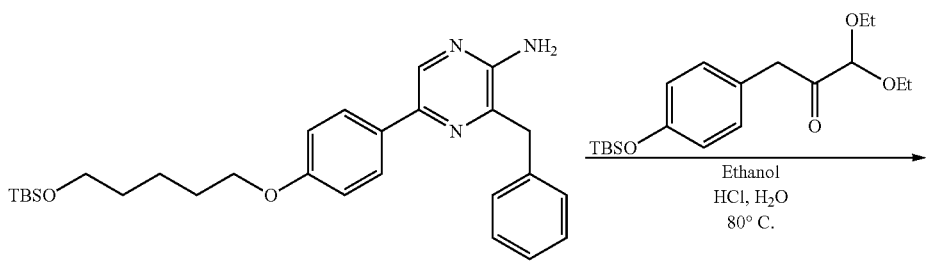

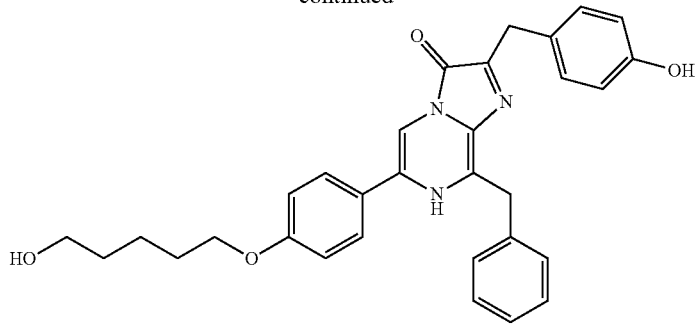

Synthesis Example 4-1

Under a nitrogen atmosphere, 4-(4,4,5,5-tetramethyl-1,3,2-dioxaborolan-2-yl)phenol (500.0 mg, 2.2 mmol, 1 eq.) and potassium carbonate (410 mg, 2.9 mmol, 1.3 eq.) were dissolved in acetone (20 ml) and the solution was stirred at room temperature. To the stirred solution were added ((5-bromopentyl)oxy)(tert-butyl)dimethylsilane (759.5 mg, 2.7 mmol, 1.2 eq.) and potassium iodide (20 mg, 0.1 mmol, 0.05 eq.) dissolved in acetone (20 ml), and the mixture was stirred at 70° C. for 7 hours. After allowing the mixture to cool to room temperature, the mixture was concentrated under reduced pressure. The resulting residue was extracted with ethyl acetate, washed with distilled water and saturated brine, dried over sodium sulfate, and then concentrated again under reduced pressure. The resulting residue was purified by flash column chromatography (eluent: hexane/ethyl acetate=9/1→8/2), to obtain tert-butyldimethyl ((5-(4-(4,4,5,5-tetramethyl-1,3,2-dioxaborolan-2-yl)phenoxy)pentyl)oxy)silane as a white solid (916 mg, 96%).

$^1$H-NMR (500 MHz, CD$_3$OD): δ (ppm)=7.73 (d, J=8.5 Hz, 2H), 6.87 (d, J=8.5 Hz, 2H), 3.98 (t, J=6.5 Hz, 2H), 3.64-3.60 (m, 2H), 1.81-1.78 (m, 2H), 1.59-1.48 (m, 4H), 1.33 (s, 12H), 0.89 (s, 9H), 0.04 (s, 6H). $^{13}$C-NMR (150 MHz, CDCl$_3$): δ (ppm)=−5.13, 18.50, 22.47, 24.99, 26.11, 29.13, 32.66, 63.15, 67.79, 83.64, 113.97, 136.61, 161.84. HR-MS: m/z calcd for C$_{23}$H$_{41}$BO$_4$Si: 421.2945, found: 421.2927 [M+H]$^+$.

Synthesis Example 4-2

Under a nitrogen atmosphere, 3-benzyl-5-bromopyrazine-2-amine (180.0 mg, 0.68 mmol, 1 eq.) and tert-butyldimethyl ((5-(4-(4,4,5,5-tetramethyl-1,3,2-dioxaborolan-2-yl)phenoxy)pentyl)oxy)silane (458.0 mg, 1.09 mmol, 1.6 eq.) were dissolved in ethanol (2 ml) and toluene (10 ml). To the solution was added 1 M aqueous sodium carbonate solution (3 ml) and the mixture was stirred at room temperature. The reaction solution was degassed under vacuum. To the solution was added a catalytic amount of tetrakis(triphenylphosphine)palladium (0) (about 1 cup of micro spatula) and the mixture was degassed again under vacuum and then stirred at 100° C. overnight (12 hours). After allowing the mixture to cool to room temperature, the mixture was filtered through Celite to remove palladium catalyst. The resulting residue was extracted with ethyl acetate, washed with distilled water and saturated brine, dried over sodium sulfate, and then concentrated under reduced pressure. The resulting residue was purified by flash column chromatography (eluent: hexane/ethyl acetate=8/2→7/3) to obtain 3-benzyl-5-(4-((5-((tert-butyldimethylsilyl)oxy)pentyl)oxy)phenyl)pyrazine-2-amine as a yellow solid (253.0 mg, 52%).

$^1$H-NMR (500 MHz, CDCl$_3$): δ (ppm)=8.32 (s, 1H), 7.86 (d, J=8.5 Hz, 2H), 7.30-7.25 (m, 5H), 6.97 (d, J=8.8 Hz, 2H), 4.34 (s, 2H), 4.17 (s, 2H), 4.01 (t, J=6.5 Hz, 2H), 3.64 (t, J=6.3 Hz, 2H), 1.84-1.81 (m, 2H), 1.61-1.57 (m, 2H), 1.54-1.51 (m, 2H), 0.90 (s, 12H), 0.06 (s, 6H). $^{13}$C-NMR (125 MHz, CDCl$_3$): δ (ppm)=−5.11, 18.51, 22.51, 26.13, 29.20, 32.70, 41.42, 63.17, 68.13, 114.95, 127.12, 128.61, 128.71, 129.10, 129.93, 136.98, 140.58, 142.87, 151.34, 159.45. (the signal for one carbon could not be assigned due to broadening) HR-MS: m/z calcd for C$_{28}$H$_{39}$N$_3$O$_2$Si: 478.2890, found: 478.2876 [M+H]$^+$.

Synthesis Example 4-3

Under an argon atmosphere, 3-benzyl-5-(4-((5-((tert-butyldimethylsilyl)oxy)pentyl)oxy)phenyl)pyrazine-2-amine (34.5 mg, 0.07 mmol, 1 eq.) and 3-(4-((tert-butyldimethylsilyl)oxy)phenyl)-1,1-diethoxypropan-2-one (55.8 mg, 0.15 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 5 hours. After allowing the mixture to cool to room temperature, the mixture was concentrated under reduced pressure, and the residue was purified by chromatography using reversed-phase HPLC columns (eluent: methanol/water=1/1+0.1% formic acid) to obtain 6-Al5OH-CTZ as a yellow solid (8.77 mg, 21%).

$^1$H-NMR (500 MHz, CD$_3$OD): δ (ppm)=7.61 (s, 1H), 7.53 (d, J=8.5 Hz, 2H), 7.38-7.14 (m, 5H), 7.15 (d, J=8.5 Hz, 2H), 6.98 (d, J=8.8 Hz, 2H), 6.69 (d, J=8.5 Hz, 2H), 4.39 (s, 2H), 4.06 (s, 2H), 4.00 (t, J=6.5 Hz, 2H), 3.57 (t, J=6.3 Hz, 2H), 1.80 (m, 2H), 1.61-1.52 (m, 6H). $^{13}$C-NMR (150 MHz, CD$_3$OD, CDCl$_3$): δ (ppm)=23.52, 30.14, 33.21, 33.36, 62.82, 69.09, 108.14, 115.95, 116.18, 128.09, 129.23, 129.39, 129.71, 129.78, 130.78, 138.24, 156.95, 161.65. HR-MS: m/z calcd for $C_{31}H_{31}N_3O_4$: 510.2393, found: 510.2376 $[M+H]^+$.

Synthesis Example 5: Synthesis of 6-Al3OMe-CTZ brine, dried over sodium sulfate, and then concentrated again under reduced pressure. The resulting residue was purified by flash column chromatography (eluent: hexane/ethyl acetate=9/1), to obtain 2-(4-(3-methoxypropoxy)phenyl)-4,4,5,5-tetramethyl-1,3,2-dioxaborolane as a white solid (287.3 mg, 73%).

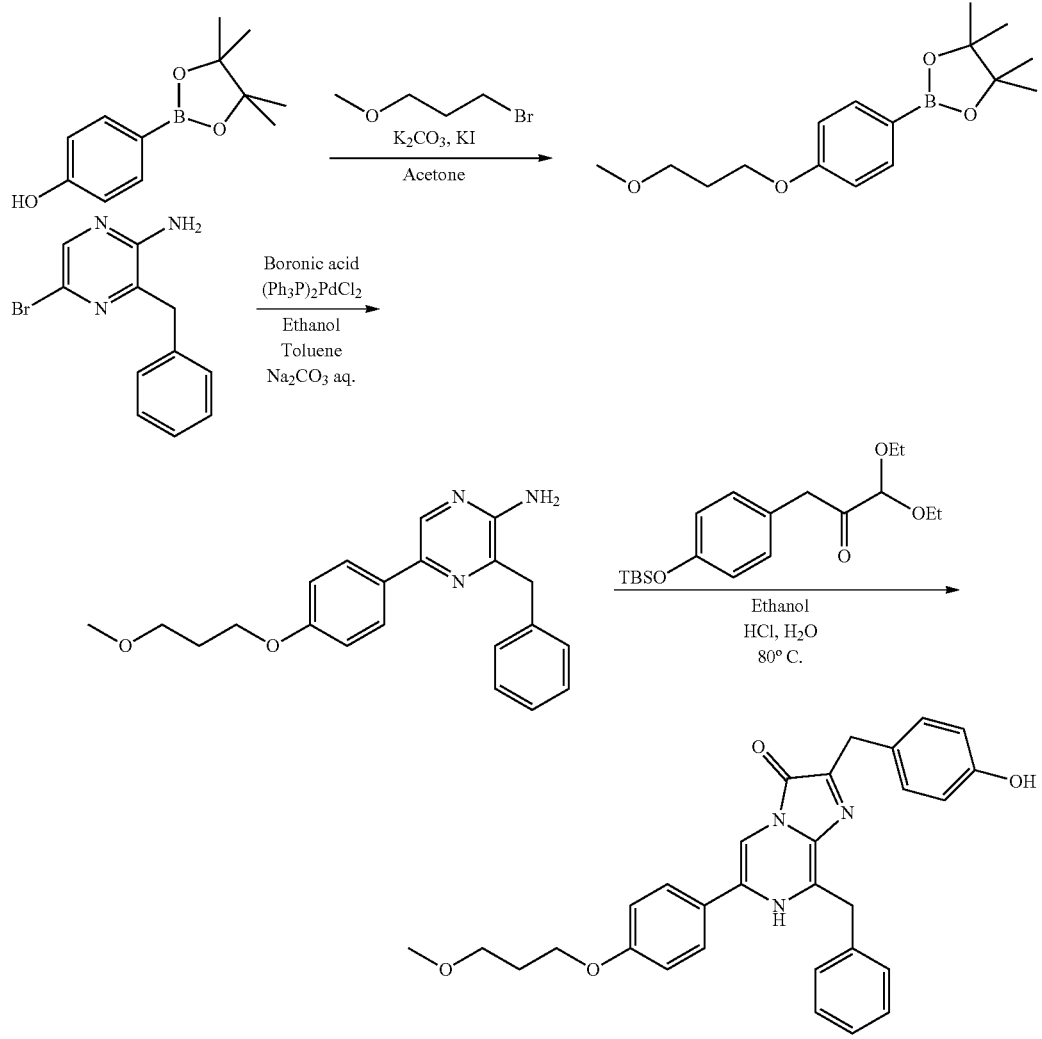

Synthesis Example 5-1 (Known Compound)

Under a nitrogen atmosphere, 4-(4,4,5,5-tetramethyl-1,3,2-dioxaborolan-2-yl)phenol (300.0 mg, 1.3 mmol, 1 eq.) and potassium carbonate (246 mg, 1.7 mmol, 1.3 eq.) were dissolved in acetone (20 ml) and the solution was stirred at room temperature. To the stirred solution were added 1-bromo-3-methoxypropane (416.2 mg, 2.7 mmol, 2 eq.) and potassium iodide (12 mg, 0.06 mmol, 0.05 eq.) dissolved in acetone (20 ml), and the mixture was stirred at 70° C. overnight (19 hours). After allowing the mixture to cool to room temperature, the mixture was concentrated under reduced pressure. The resulting residue was extracted with ethyl acetate, washed with distilled water and saturated Synthesis Example 5-2

Under a nitrogen atmosphere, 3-benzyl-5-bromopyrazine-2-amine (100.0 mg, 0.3 mmol, 1 eq.) and 2-(4-(3-methoxypropoxy)phenyl)-4,4,5,5-tetramethyl-1,3,2-dioxaborolane (176.9 mg, 0.6 mmol, 2 eq.) were dissolved in ethanol (1 ml) and toluene (6 ml). To the solution was added 1 M aqueous sodium carbonate solution (1.6 ml) and the mixture was stirred at room temperature. The reaction solution was degassed under vacuum. To the solution was added a catalytic amount of tetrakis(triphenylphosphine)palladium (0) (about 1 cup of micro spatula) and the mixture was degassed again under vacuum and then stirred at 100° C. overnight (12 hours). After allowing the mixture to cool to room temperature, the mixture was filtered through Celite to remove palladium catalyst. The resulting residue was extracted with ethyl acetate, washed with distilled water and saturated brine, dried over sodium sulfate, and then concentrated under reduced pressure. The resulting residue was purified by flash column chromatography (eluent: hexane/ethyl acetate=7/3→1/1) to obtain 3-benzyl-5-(4-(3-methoxypropoxy)phenyl)pyrazine-2-amine as a yellow solid (127.3 mg, 96%).

$^1$H-NMR (500 MHz, CD$_3$OD): δ (ppm)=8.32 (s, 1H), 7.86 (d, J=8.3 Hz, 2H), 7.33-7.26 (m, 5H), 6.98 (d, J=8.8 Hz, 2H), 4.34 (s, 2H), 4.17 (s, 2H) 4.11 (t, J=6.0 Hz, 2H), 3.58 (t, J=6.3 Hz, 2H), 1.33 (m, 12H), 0.90 (s, 9H), 0.09 (s, 6H). $^{13}$C-NMR (150 MHz, CDCl$_3$): δ (ppm)=29.75, 41.38, 58.87, 65.06, 69.36, 114.95, 127.11, 128.58, 128.70, 129.08, 130.04, 132.26, 136.97, 140.57, 142.77, 151.36, 139.31.

Synthesis Example 5-3

Under an argon atmosphere, 3-benzyl-5-(4-(3-methoxypropoxy)phenyl)pyrazine-2-amine (35.0 mg, 0.1 mmol, 1 eq.) and 3-(4-((tert-butyldimethylsilyl)oxy)phenyl)-1,1-diethoxypropan-2-one (70.5 mg, 0.2 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 6 hours. After allowing the mixture to cool to room temperature, the mixture was concentrated under reduced pressure, and the residue was purified by silica column chromatography (methylene chloride/methanol=20/1) to obtain 6-Al3OMe-CTZ as a yellow solid (18.2 mg, 52%).

$^1$H-NMR (500 MHz, CD$_3$OD): δ (ppm)=7.61 (s, 1H), 7.47 (d, J=5.1 Hz, 2H), 7.36 (d, J=7.4 Hz, 2H), 7.27-7.12 (m, 5H), 6.92 (d, J=6.3 Hz, 2H), 6.67 (d, J=7.1 Hz, 2H), 4.36 (s, 2H), 4.03 (s, 4H), 3.53 (t, J=6.3 Hz, 2H), 3.33 (s, 3H), 2.02-1.97 (m, 2H). $^{13}$C-NMR (150 MHz, CD$_3$OD): δ (ppm)= 30.50, 33.19, 35.16, 58.91, 66.04, 70.29, 108.15, 115.66, 115.91, 116.21, 127.84, 128.14, 129.20, 129.55, 129.74, 12977, 130.63, 130.79, 138.08, 156.99, 161.53.

Synthesis Example 6: Synthesis of 6-Al2N3-CTZ

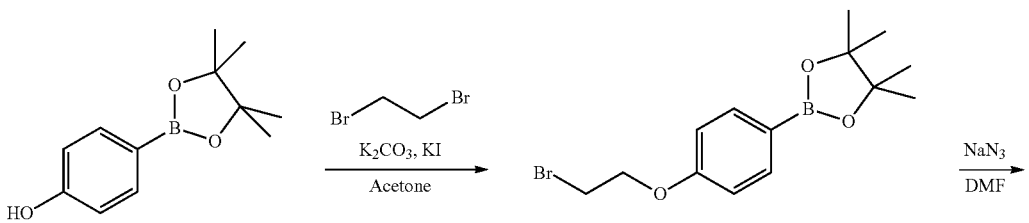

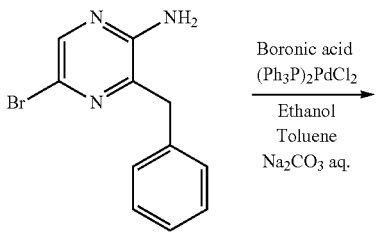

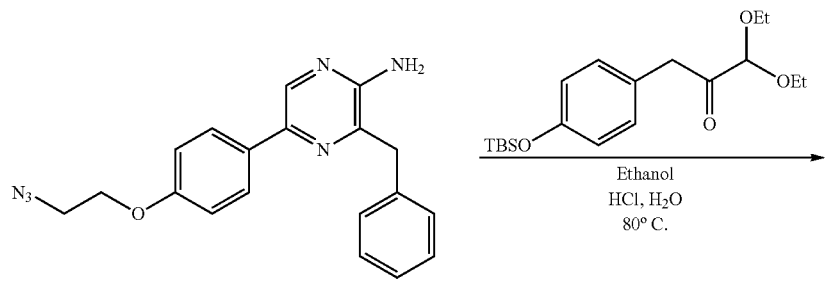

-continued

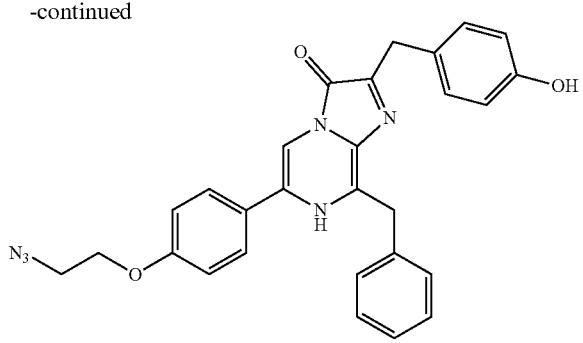

Synthesis Example 6-1 (Known Compound)

Under a nitrogen atmosphere, 4-(4,4,5,5-tetramethyl-1,3,2-dioxaborolan-2-yl)phenol (1.0 g, 4.5 mmol, 1 eq.) and potassium carbonate (0.82 g, 5.9 mmol, 1.3 eq.) were dissolved in acetone (20 ml) and the solution was stirred at room temperature. To the stirred solution were added 1,2-dibromoethane (4.1 g, 22.7 mmol, 22.7 eq.) and potassium iodide (0.02 g, 0.1 mmol, 0.02 eq.) dissolved in acetone (20 ml), and the mixture was stirred at 70° C. overnight (16 hours). After allowing the mixture to cool to room temperature, the mixture was concentrated under reduced pressure. The resulting residue was extracted with methylene chloride, washed with distilled water and saturated brine, dried over sodium sulfate, and then concentrated again under reduced pressure. The resulting residue was purified by flash column chromatography (eluent: chloroform→chloroform/methanol=49/1), to obtain 2-(4-(2-bromoethoxy)phenyl)-4,4,5,5-tetramethyl-1,3,2-dioxaborolane as a white solid (359.0 mg, 24%).

Synthesis Example 6-2 (Known Compound)

Under a nitrogen atmosphere, 2-(4-(2-bromoethoxy)phenyl)-4,4,5,5-tetramethyl-1,3,2-dioxaborolane (350 mg, 1.0 mmol, 1.0 eq.) was dissolved in N,N-dimethyl formamide (10 ml). To the solution was added sodium azide (83 mg, 1.2 mmol, 1.2 eq.), and the mixture was stirred at 100° C. for 1 hour. After completion of the reaction, the resultant was extracted with toluene, washed with distilled water and saturated brine, dried over sodium sulfate, and then concentrated under reduced pressure. This gave 2-(4-(2-azidoethoxy)phenyl)-4,4,5,5-tetramethyl-1,3,2-dioxaborolane as a white solid (299.0 mg, 97%).

Synthesis Example 6-3

Under a nitrogen atmosphere, 3-benzyl-5-bromopyrazine-2-amine (250.0 mg, 0.9 mmol, 1 eq.) and 2-(4-(2-azidoethoxy)phenyl)-4,4,5,5-tetramethyl-1,3,2-dioxaborolane (358.0 mg, 1.2 mmol, 1.6 eq.) were dissolved in ethanol (1 ml) and toluene (6 ml). To the solution was added 1 M aqueous sodium carbonate solution (2.0 ml) and the mixture was stirred at room temperature. The reaction solution was degassed under vacuum. To the solution was added a catalytic amount of tetrakis(triphenylphosphine)palladium (0) (about 1 cup of micro spatula) and the mixture was degassed again under vacuum and then stirred at 100° C. overnight (17 hours). After allowing the mixture to cool to room temperature, the mixture was filtered through Celite to remove palladium catalyst. The resulting residue was extracted with ethyl acetate, washed with distilled water and saturated brine, dried over sodium sulfate, and then concentrated under reduced pressure. The resulting residue was purified by flash column chromatography (eluent: chloroform/ethyl acetate=19/1→9/1) to obtain 5-(4-(2-azidoethoxy)phenyl)-3-benzylpyrazine-2-amine as a yellow solid (122.0 mg, 50%).

$^1$H-NMR (500 MHz, CDCl$_3$): δ (ppm)=8.33 (s, 1H), 7.89 (d, J=8.8 Hz, 2H), 7.34-7.26 (m, 5H), 7.01 (d, J=8.5 Hz, 2H), 4.35 (s, 2H), 4.21 (t, J=4.8 Hz, 2H), 4.18 (s, 2H), 3.63 (t, J=4.8 Hz, 2H). $^{13}$C-NMR (150 MHz, CDCl$_3$): δ (ppm)= 41.37, 50.29, 67.14, 115.02, 127.16, 127.21, 128.69, 129.10, 130.82, 136.91, 137.04, 140.61, 142.48, 151.49, 158.47.

Synthesis Example 6-4

Under an argon atmosphere, 5-(4-(2-azidoethoxy)phenyl)-3-benzylpyrazine-2-amine (121.0 mg, 0.3 mmol, 1 eq.) and 3-(4-((tert-butyldimethylsilyl)oxy)phenyl)-1,1-diethoxypropan-2-one (197.0 mg, 0.5 mmol, 1.6 eq.) were dissolved in ethanol (10 ml) and milliQ (1.0 ml) and the mixture was cooled to 0° C. The reaction solution was degassed under vacuum, concentrated hydrochloric acid (0.5 ml) was added, and then the mixture was stirred at 80° C. overnight (15 hours). After allowing the mixture to cool to room temperature, the mixture was concentrated under reduced pressure, and the residue was purified by silica column chromatography (ethyl acetate/methanol=20/1) to obtain 6-Al2N3-CTZ as a yellow solid (29.0 mg, 17%).

$^1$H-NMR (500 MHz, CD$_3$OD): δ (ppm)=8.09 (s, 1H), 7.75 (d, J=7.7 Hz, 2H), 7.39-7.22 (m, 5H), 7.12 (d, J=8.5 Hz, 2H), 7.08 (d, J=8.8 Hz, 2H), 6.71 (d, J=8.3 Hz, 2H), 4.47 (s, 2H), 4.22 (t, J=4.5 Hz, 2H), 4.13 (s, 2H), 3.62 (t, J=4.5 Hz, 2H). $^{13}$C-NMR (150 MHz, CD$_3$OD, CDCl$_3$): δ (ppm)= 33.14, 35.08, 51.05, 68.24, 108.14, 115.90, 116.05, 127.97, 129.13, 129.55, 129.62, 130.47, 130.62, 137.75, 156.56, 160.59.

Synthesis Example 7: Synthesis of 6-Alkyl3CTZ

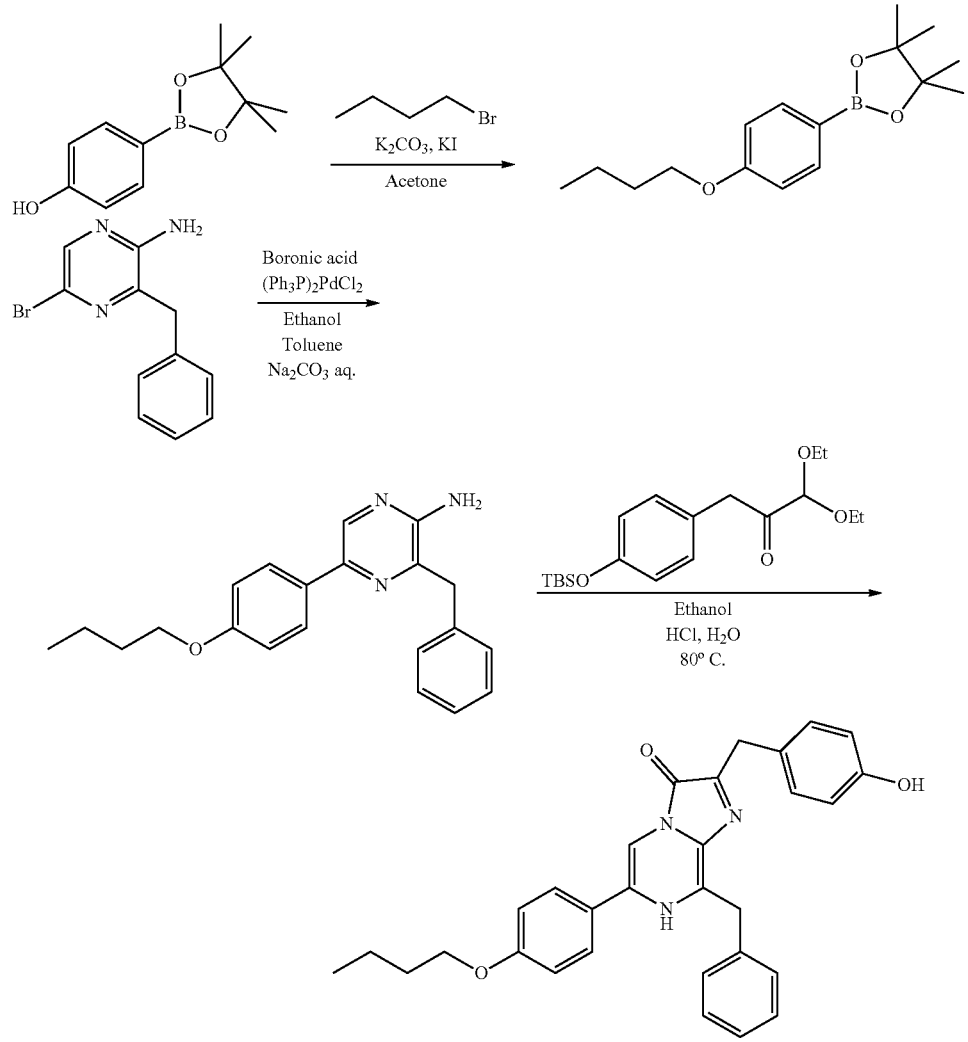

Synthesis Example 7-1 (Known Compound)

Under a nitrogen atmosphere, 4-(4,4,5,5-tetramethyl-1,3,2-dioxaborolan-2-yl)phenol (500.0 mg, 2.2 mmol, 1 eq.) and potassium carbonate (410 mg, 2.9 mmol, 1.3 eq.) were dissolved in acetone (20 ml) and the solution was stirred at room temperature. To the stirred solution were added 1-bromobutane (622.6 mg, 4.5 mmol, 2 eq.) and potassium iodide (0.02 g, 0.1 mmol, 0.02 eq.) dissolved in acetone (20 ml), and the mixture was stirred at 70° C. overnight (12 hours). After allowing the mixture to cool to room temperature, the mixture was concentrated under reduced pressure. The resulting residue was extracted with ethyl acetate, washed with distilled water and saturated brine, dried over sodium sulfate, and then concentrated again under reduced pressure. This gave a crude product of 2-(4-butoxyphenyl)-4,4,5,5-tetramethyl-1,3,2-dioxaborolane as a white solid. The crude product was used directly in the next reaction step without further purification.

Synthesis Example 7-2

Under a nitrogen atmosphere, 3-benzyl-5-bromopyrazine-2-amine (100.0 mg, 0.3 mmol, 1 eq.) and 2-(4-butoxyphenyl)-4,4,5,5-tetramethyl-1,3,2-dioxaborolane (167.0 mg, 0.4 mmol, 1.6 eq.) were dissolved in ethanol (1 ml) and toluene (6 ml). To the solution was added 1 M aqueous sodium carbonate solution (2.0 ml) and the mixture was stirred at room temperature. The reaction solution was degassed under vacuum. To the solution was added a catalytic amount of tetrakis(triphenylphosphine)palladium (0) (about 1 cup of micro spatula) and the mixture was degassed again under vacuum and then stirred at 100° C. overnight (13 hours). After allowing the mixture to cool to room temperature, the mixture was filtered through Celite to remove palladium catalyst. The resulting residue was extracted with ethyl acetate, washed with distilled water and saturated brine, dried over sodium sulfate, and then concentrated under reduced pressure. The resulting residue was purified by flash column chromatography (eluent: hexane/ethyl acetate=4/1→7/3) to obtain 3-benzyl-5-(4-butoxyphenyl)pyrazine-2-amine as a yellow solid (121.6 mg, 96%).

$^1$H-NMR (500 MHz, CDCl$_3$): δ (ppm)=8.33 (s, 1H), 7.86 (d, J=8.8 Hz, 2H), 7.33-7.23 (m, 5H), 6.98 (d, J=8.8 Hz, 2H), 4.34 (s, 2H), 4.17 (s, 2H), 4.01 (t, J=6.5 Hz, 2H), 1.79 (m, 2H), 1.52 (m, 2H), 0.99 (t, J=7.4 Hz, 2H). $^{13}$C-NMR (150 MHz, CDCl$_3$): δ (ppm)=14.02, 19.39, 31.45, 41.42, 67.92, 114.95, 127.12, 127.15, 128.71, 129.10, 129.89, 136.99, 140.58, 142.87, 151.34, 159.48.

Synthesis Example 7-3

Under an argon atmosphere, 3-benzyl-5-(4-butoxyphenyl)pyrazine-2-amine (30.0 mg, 0.08 mmol, 1 eq.) and 3-(4-((tert-butyldimethylsilyl)oxy)phenyl)-1,1-diethoxypropan-2-one (63.4 mg, 0.17 mmol, 2.0 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 6 hours. After allowing the mixture to cool to room temperature, the mixture was concentrated under reduced pressure, and the residue was purified by silica column chromatography (methylene chloride/methanol=20/1) to obtain 6-Alkyl3-CTZ as a yellow solid (12.8 mg, 30%).

$^1$H-NMR (500 MHz, CD$_3$OD, CDCl$_3$): δ (ppm)=7.57 (s, 1H), 7.51 (d, J=8.0 Hz, 2H), 7.41 (d, J=8.3 Hz, 2H), 7.31-7.18 (m, 5H), 6.98 (d, J=8.5 Hz, 2H), 6.72 (d, J=8.5 Hz, 2H), 4.39 (s, 2H), 4.10 (s, 2H), 4.02 (t, J=6.3 Hz, 2H), 1.81-1.75 (m, 2H), 1.54-1.49 (m, 2H), 1.00 (t, J=7.4 Hz, 3H). $^{13}$C-NMR (150 MHz, CD$_3$OD, CDCl$_3$): δ (ppm) =14.09, 19.87, 31.95, 68.55, 107.73, 115.64, 115.90, 127.83, 128.78, 129.39, 129.43, 130.39, 137.39, 156.22, 161.15.

Synthesis Example 8: Synthesis of 6-Al2OH-2H-CTZ

Under an argon atmosphere, 3-benzyl-5-(4-(2-((tert-butyldimethylsilyl)oxy)ethoxy)phenyl)pyrazine-2-amine (71.3 mg, 0.16 mmol, 1 eq.) and 1,1-diethoxy-3-phenylpropan-2-one (72.7 mg, 0.32 mmol, 2 eq.) were dissolved in ethanol (4 ml) and milliQ (0.4 ml) and the mixture was cooled to 0° C. The reaction solution was degassed under vacuum, concentrated hydrochloric acid (0.2 ml) was added, and then the mixture was stirred at 80° C. for 14 hours. After allowing the mixture to cool to room temperature, the mixture was concentrated under reduced pressure, and the residue was purified by silica column chromatography (methylene chloride/methanol=20/1) to obtain 6-Al2OH-2H-CTZ as a yellow solid (17.9 mg, 24%).

$^1$H-NMR (500 MHz, CD$_3$OD): δ (ppm)=7.69 (s, 1H), 7.51 (d, J=7.7 Hz, 2H), 7.37 (d, J=7.7 Hz, 2H), 7.29-7.11 (m, 8H), 6.97 (d, J=8.5 Hz, 2H) 4.38 (s, 2H), 4.13 (s, 2H), 4.04 (t, J=4.5 Hz, 2H), 3.87 (t, J=5.1 Hz, 2H). $^{13}$C-NMR (150 MHz, CD$_3$OD, CDCl$_3$): δ (ppm)=33.78, 33.36, 35.39, 61.56, 70.72, 108.51, 116.02, 126.15, 127.44, 127.85, 128.21, 129.27, 129.48, 129.76, 129.81, 132.36, 137.87, 139.71, 161.61. HR-MS: m/z calcd for C$_{28}$H$_{25}$N$_3$O$_3$: 452.1974, found: 452.1968 [M+H]$^+$.

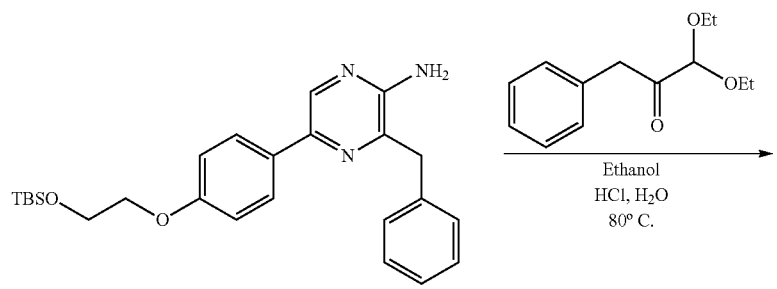

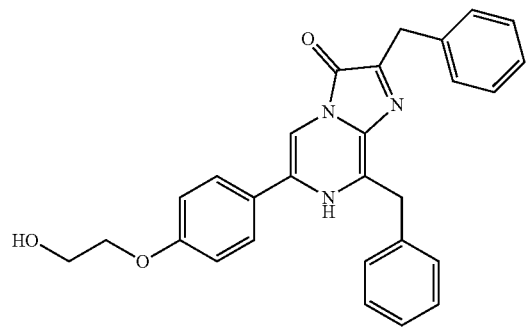

Synthesis Example 9: Synthesis of 6-Al3OH-2H-CTZ

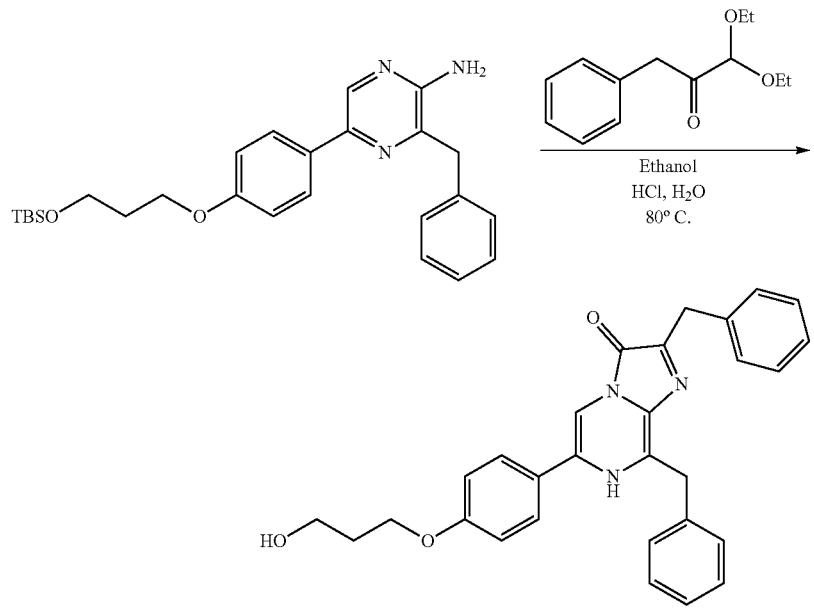

Under an argon atmosphere, 3-benzyl-5-(4-(3-((tert-butyldimethylsilyl)oxy)propoxy)phenyl)pyrazine-2-amine (20.0 mg, 0.04 mmol, 1 eq.) and 1,1-diethoxy-3-phenylpropan-2-one (19.7 mg, 0.08 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 14 hours. After allowing the mixture to cool to room temperature, the mixture was concentrated under reduced pressure, and the residue was purified by silica column chromatography (methylene chloride/methanol=20/1→10/1) to obtain 6-Al3OH-2H-CTZ as a yellow solid (9.38 mg, 45%).

$^1$H-NMR (500 MHz, CD$_3$OD): δ (ppm)=7.60 (s, 1H), 7.52 (s, 2H), 7.38-7.14 (m, 10H), 6.99 (d, J=8.0 Hz, 2H), 4.39 (s, 2H), 4.16 (s, 2H), 4.09 (t, J=6.0 Hz, 2H), 3.73 (t, J=6.3 Hz, 2H), 1.98 (q, J=6.0 Hz, 2H). $^{13}$C-NMR (150 MHz, CD$_3$OD, CDCl$_3$): δ (ppm)=18.36, 33.27, 116.00, 128.19, 129.30, 129.48, 129.77, 129.82, 138.04, 139.91, 161.71. HR-MS: m/z calcd for C$_{29}$H$_{27}$N$_3$O$_3$: 466.2131, found: 466.2112 [M+H]$^+$.

Synthesis Example 10: Synthesis of 6-Al4OH-2H-CTZ

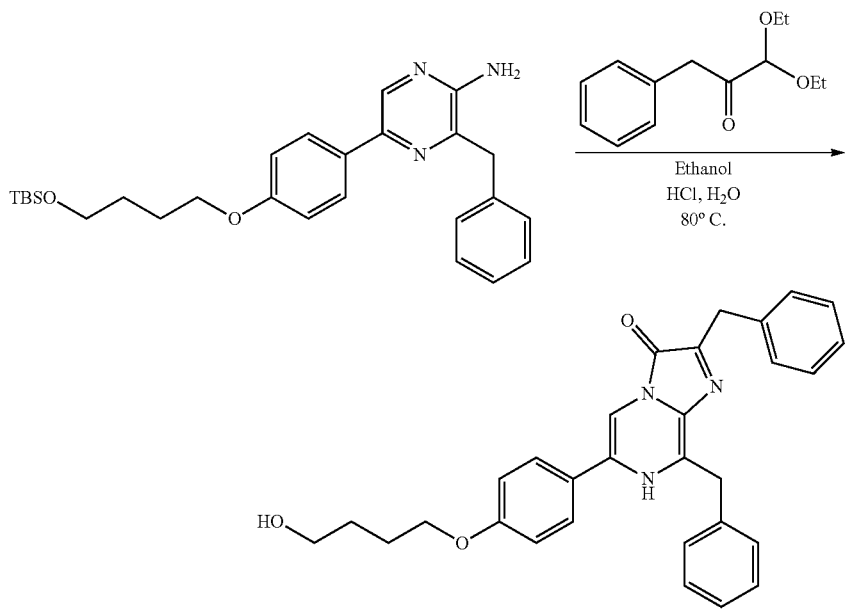

3-benzyl-5-(4-(4-((tert-butyldimethylsilyl)oxy)butoxy) phenyl)pyrazine-2-amine (35.0 mg, 0.08 mmol, 1 eq.) and 1,1-diethoxy-3-phenylpropan-2-one (35.7 mg, 0.16 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 13.5 hours. After allowing the mixture to cool to room temperature, the mixture was concentrated under reduced pressure, and the residue was purified by silica column chromatography (methylene chloride/methanol=20/1) to obtain 6-Al4OH-2H-CTZ as a yellow solid (7.73 mg, 20%).

$^1$H-NMR (500 MHz, CD$_3$OD): δ (ppm)=7.61 (s, 1H), 7.51 (s, 2H), 7.38-7.14 (m, 10H), 6.97 (d, J=7.1 Hz, 2H), 4.38 (s, 2H), 4.15 (s, 2H), 4.02 (t, J=6.0 Hz, 2H), 3.61 (t, J=6.3 Hz, 2H), 1.87-182 (m, 2H), 1.72-1.67 (m, 2H). $^{13}$C-NMR (150 MHz, CD$_3$OD, CDCl$_3$): δ (ppm)=26.86, 30.17, 62.60, 69.01, 108.20, 115.98, 127.39, 128.19, 129.29, 129.48, 129.77, 129.82, 138.03, 139.91, 161.71. HR-MS: m/z calcd for C$_{30}$H$_{29}$N$_3$O$_3$: 480.2287, found: 480.2265 [M+H]$^+$.

Synthesis Example 11: Synthesis of 6-Al5OH-2H-CTZ 3-benzyl-5-(4-((5-((tert-butyldimethylsilyl)oxy)pentyl) oxy)phenyl)pyrazine-2-amine (35.0 mg, 0.08 mmol, 1 eq.) and 1,1-diethoxy-3-phenylpropan-2-one (35.7 mg, 0.16 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 13.5 hours. After allowing the mixture to cool to room temperature, the mixture was concentrated under reduced pressure, and the residue was purified by silica column chromatography (methylene chloride/methanol=10/1) to obtain 6-Al5OH-2H-CTZ as a yellow solid (5.81 mg, 14%).

$^1$H-NMR (500 MHz, CD$_3$OD): δ (ppm)=7.62 (s, 1H), 7.54 (d, J=7.1 Hz, 2H), 7.39-7.15 (m, 10H), 6.99 (d, J=8.0 Hz, 2H), 4.39 (s, 2H), 4.16 (s, 2H), 4.01 (t, J=6.0 Hz, 2H), 3.57 (t, J=6.5 Hz, 2H), 1.83-1.79 (m, 2H), 1.62-1.52 (m, 4H). $^{13}$C-NMR (150 MHz, CD$_3$OD, CDCl$_3$): δ (ppm)= 23.53, 30.14, 33.36, 62.82, 69.12, 108.19, 116.00, 127.39, 128.19, 129.31, 129.48, 129.56, 129.77, 129.83, 131.37, 138.05, 139.93, 161.78. HR-MS: m/z calcd for C$_{31}$H$_{31}$N$_3$O$_3$: 494.2444, found: 494.2415 [M+H]$^+$.

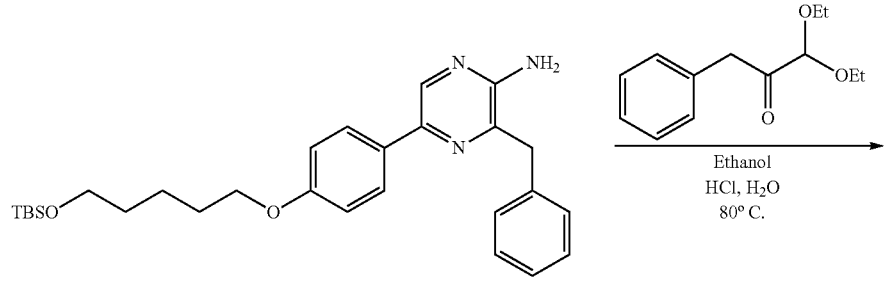

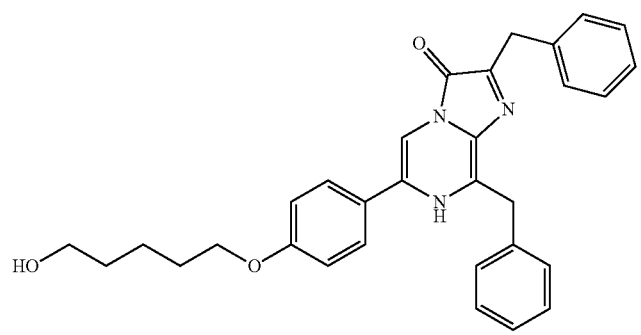

Synthesis Example 12: Synthesis of 6-Al3OMe-2H-CTZ

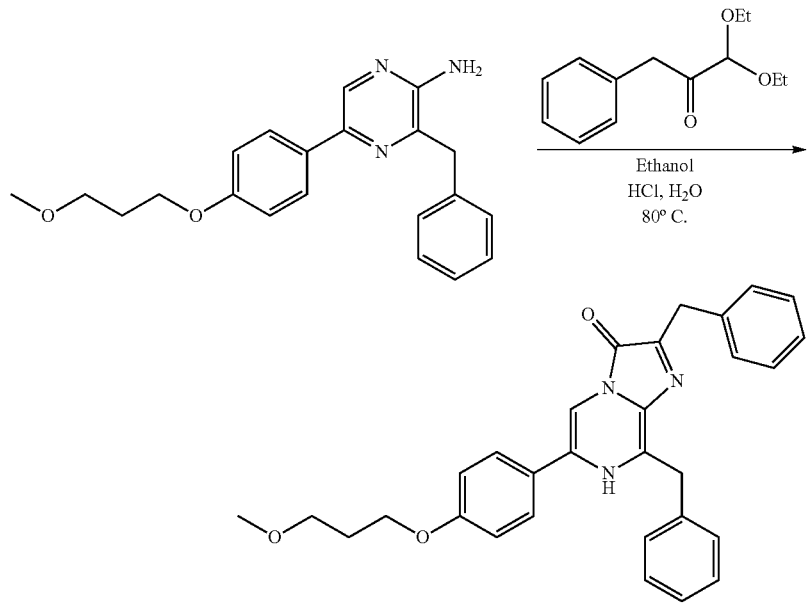

Under an argon atmosphere, 3-benzyl-5-(4-(3-methoxypropoxy)phenyl)pyrazine-2-amine (30.0 mg, 0.08 mmol, 1 eq.) and 1,1-diethoxy-3-phenylpropan-2-one (38.0 mg, 0.17 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. overnight (16 hours). After allowing the mixture to cool to room temperature, the mixture was concentrated under reduced pressure, and the residue was purified by silica column chromatography (methylene chloride/methanol=20/1) to obtain 6-Al3OMe-2H-CTZ as a yellow solid (22.6 mg, 55%).

$^1$H-NMR (500 MHz, CD$_3$OD, CDCl$_3$): δ (ppm)=7.54 (s, 1H), 7.47 (d, J=8.5 Hz, 2H), 7.38 (d, J=7.4 Hz, 2H), 7.32 (d, J=7.4 Hz, 2H), 7.27-7.12 (m, 6H), 6.93 (d, J=8.8 Hz, 2H), 4.36 (s, 2H), 4.15 (s, 2H), 4.03 (t, J=6.3 Hz, 2H), 3.54 (t, J=6.0 Hz, 2H), 3.33 (s, 3H), 2.03-1.98 (m, 2H). $^{13}$C-NMR (150 MHz, CD$_3$OD, CDCl$_3$): (ppm)=30.36, 34.06, 34.96, 58.91, 65.90, 70.06, 108.09, 115.83, 125.75, 127.24, 127.72, 128.06, 129.32, 129.61, 129.66, 129.69, 137.76, 139.65, 152.49, 161.35.

Synthesis Example 13: Synthesis of 6-Alkyl3-2H-CTZ

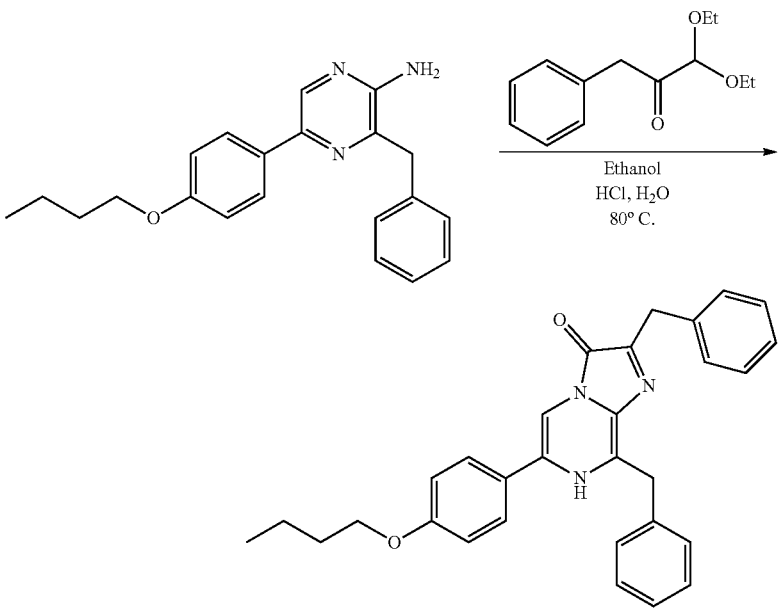

Under an argon atmosphere, 3-benzyl-5-(4-butoxyphenyl)pyrazine-2-amine (32.7 mg, 0.09 mmol, 1 eq.) and 1,1-diethoxy-3-phenylpropan-2-one (43.7 mg, 0.19 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. overnight (21 hours). After allowing the mixture to cool to room temperature, the mixture was concentrated under reduced pressure, and the residue was purified by silica column chromatography (methylene chloride/methanol=20/1) to obtain 6-Alkyl3-2H-CTZ as a yellow solid (27.4 mg, 60%).

$^1$H-NMR (500 MHz, CD$_3$OD, CDCl$_3$): S (ppm)=7.45 (s, 1H), 7.48 (d, J=8.3 Hz, 2H), 7.39 (d, J=7.3 Hz, 2H), 7.33 (d, J=7.4 Hz, 2H), 7.28-7.13 (m, 6H), 6.94 (d, J=8.8 Hz, 2H), 4.38 (s, 2H), 4.16 (s, 2H), 3.96 (t, J=6.5 Hz, 2H), 1.78-1.72 (m, 2H), 1.52-1.47 (m, 2H), 0.97 (t, J=7.4 Hz, 3H). $^{13}$C-NMR (150 MHz, CD$_3$OD, CDCl$_3$): S (ppm)=14.15, 20.08, 32.18, 34.08, 34.84, 68.71, 107.99, 115.79, 127.19, 128.03, 129.01, 129.27, 129.58, 129.61, 129.65, 137.69, 139.55, 161.46.

Synthesis Example 14: Synthesis of 6-Ethyl-CTZ

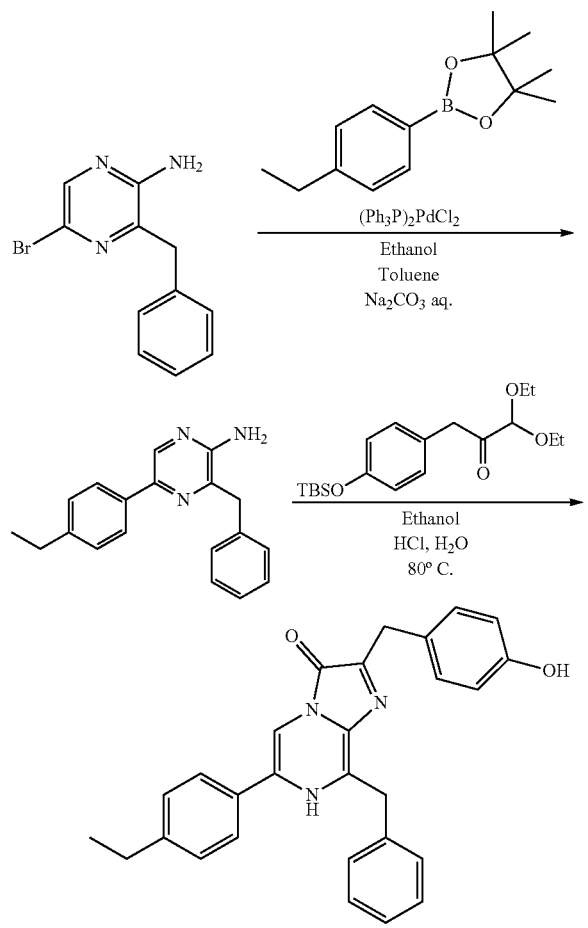

Synthesis Example 14-1

Under a nitrogen atmosphere, 3-benzyl-5-bromopyrazine-2-amine (100.0 mg, 0.3 mmol, 1 eq.) and 2-(4-ethylphenyl)-4,4,5,5-tetramethyl-1,3,2-dioxaborolane (140.4 mg, 0.6 mmol, 1.6 eq.) were dissolved in ethanol (1 ml) and toluene (6 ml). To the solution was added 1 M aqueous sodium carbonate solution (1.6 ml) and the mixture was stirred at room temperature. The reaction solution was degassed under vacuum. To the solution was added a catalytic amount of tetrakis(triphenylphosphine)palladium (0) (about 1 cup of micro spatula) and the mixture was degassed again under vacuum and then stirred at 100° C. overnight (12 hours). After allowing the mixture to cool to room temperature, the mixture was filtered through Celite to remove palladium catalyst. The resulting residue was extracted with ethyl acetate, washed with distilled water and saturated brine, dried over sodium sulfate, and then concentrated under reduced pressure. The resulting residue was purified by flash column chromatography (eluent: hexane/ethyl acetate=7/3) to obtain 3-benzyl-5-(4-ethylphenyl)pyrazine-2-amine as a yellow solid (100.4 mg, 0.3 mmol, 91%).

$^1$H-NMR (500 MHz, CDCl$_3$): δ (ppm)=8.37 (s, 1H), 7.86 (d, J=8.0 Hz, 2H), 7.33-7.25 (m, 7H), 4.37 (s, 2H), 4.18 (s, 2H), 2.70 (t, J=7.4 Hz, 2H), 1.28-1.25 (m, 3H). $^{13}$C-NMR (150 MHz, CDCl$_3$): δ (ppm)=15.78, 28.79, 41.42, 76.90, 77.16, 77.41, 125.91, 127.16, 128.48, 128.71, 129.11, 134.87, 136.95, 137.44, 140.67, 142.96, 144.47, 151.66.

Synthesis Example 14-2

Under an argon atmosphere, 3-benzyl-5-(4-ethylphenyl)pyrazine-2-amine (30.0 mg, 0.1 mmol, 1 eq.) and 3-(4-((tert-butyldimethylsilyl)oxy)phenyl)-1,1-diethoxypropan-2-one (72.6 mg, 0.20 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. overnight (21 hours). After allowing the mixture to cool to room temperature, the mixture was concentrated under reduced pressure, and the residue was purified by silica column chromatography (methylene chloride/methanol=20/1) to obtain 6-Ethyl-CTZ as a yellow solid (9.6 mg, 21%).

$^1$H-NMR (500 MHz, CD$_3$OD): δ (ppm)=7.65 (s, 1H), 7.53 (d, J=7.1 Hz, 2H), 7.38 (d, J=7.7 Hz, 2H), 7.30-7.20 (m, 5H), 7.15 (d, J=8.3 Hz, 2H), 6.69 (d, J=8.3 Hz, 2H), 4.39 (s, 2H), 4.06 (2H), 2.68 (q, J=7.4 Hz, 2H), 1.22 (q, J=7.4 Hz, 3H). $^{13}$C-NMR (150 MHz, CD$_3$OD): δ (ppm)=15.98, 29.58, 33.27, 108.54, 116.21, 127.87, 128.18, 129.58, 129.76, 130.59, 130.80, 138.06, 147.38, 157.01.

Synthesis Example 15: Synthesis of 6-Ethyl-2H-CTZ

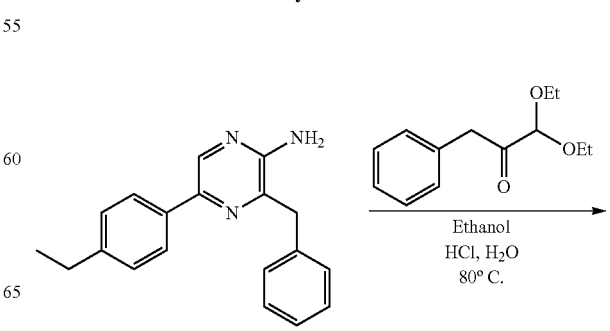

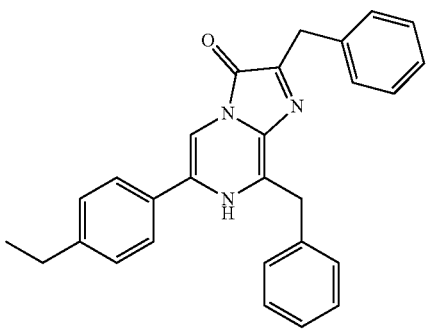
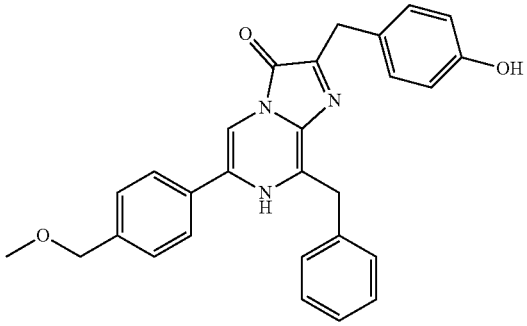

Under an argon atmosphere, 3-benzyl-5-(4-ethylphenyl) pyrazine-2-amine (35.7 mg, 0.12 mmol, 1 eq.) and 1,1-diethoxy-3-phenylpropan-2-one (54.9 mg, 0.24 mmol, 2 eq.) were dissolved in ethanol (3 ml) and milliQ (0.3 ml) and the mixture was cooled to 0° C. The reaction solution was degassed under vacuum, concentrated hydrochloric acid (0.15 ml) was added, and then the mixture was stirred at 80° C. overnight (14 hours). After allowing the mixture to cool to room temperature, the mixture was concentrated under reduced pressure, and the residue was purified by silica column chromatography (methylene chloride/methanol=20/1) to obtain 6-Ethyl-2H-CTZ as a yellow solid (48.85 mg, 94%).

$^{1}$H-NMR (500 MHz, CD$_{3}$OD, CDCl$_{3}$): δ (ppm)=7.48 (s, 1H), 7.41 (d, J=7.4 Hz, 2H), 7.35 (d, J=7.1 Hz, 2H), 7.30-7.15 (m, 10H), 4.39 (s, 2H), 4.19 (s, 2H), 2.65 (q, J=7.4 Hz, 2H), 1.23 (q, J=7.7 Hz, 3H). $^{13}$C-NMR (150 MHz, CD$_{3}$OD, CDCl$_{3}$): δ (ppm)=15.68, 29.07, 34.00, 34.48, 108.07, 124.81, 126.74 126.85, 127.14, 127.25, 127.72, 128.20, 128.42, 128.70, 128.93, 129.05, 129.24, 129.27, 129.30, 136.42, 137.00, 138.94, 146.65.

Synthesis Example 16: Synthesis of 6-Ether-CTZ (Comparative Compound)

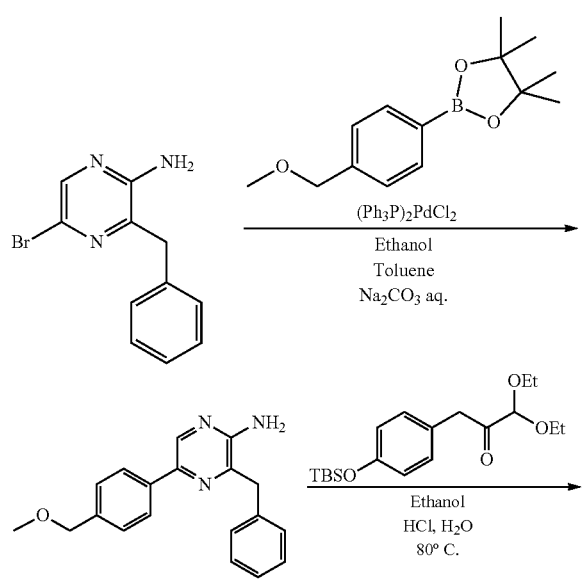

Synthesis Example 16-1

Under a nitrogen atmosphere, 3-benzyl-5-bromopyrazine-2-amine (166.0 mg, 0.6 mmol, 1 eq.) and 2-(4-(methoxymethyl)phenyl)-4,4,5,5-tetramethyl-1,3,2-dioxaborolane (249.5 mg, 1.0 mmol, 1.6 eq.) were dissolved in ethanol (2 ml) and toluene (12 ml). To the solution was added 1 M aqueous sodium carbonate solution (3 ml) and the mixture was stirred at room temperature. The reaction solution was degassed under vacuum. To the solution was added a catalytic amount of tetrakis(triphenylphosphine)palladium (0) (about 1 cup of micro spatula) and the mixture was degassed again under vacuum and then stirred at 100° C. overnight (13 hours). After allowing the mixture to cool to room temperature, the mixture was filtered through Celite to remove palladium catalyst. The resulting residue was extracted with ethyl acetate, washed with distilled water and saturated brine, dried over sodium sulfate, and then concentrated under reduced pressure. The resulting residue was purified by flash column chromatography (eluent: hexane/ethyl acetate=1/2→1/1) to obtain 3-benzyl-5-(4-(methoxymethyl)phenyl)pyrazine-2-amine as a yellow solid (169.5 mg, 0.5 mmol, 88%).

$^{1}$H-NMR (500 MHz, CDCl$_{3}$): δ (ppm)=8.39 (s, 1H), 7.93 (d, J=8.3 Hz, 2H), 7.42 (d, J=8.3 Hz, 2H), 7.43-7.25 (m, 5H), 4.51 (s, 2H), 4.42 (s, 2H), 4.19 (s, 2H), 3.4 (s, 2H). $^{13}$C-NMR (150 MHz, CDCl$_{3}$): δ (ppm)=41.42, 58.18, 74.53, 76.90, 77.16, 77.41, 125.91, 127.21, 128.33, 128.71, 129.13, 136.85, 137.65, 138.17, 140.74, 142.51, 151.88.

Synthesis Example 16-2

Under an argon atmosphere, 3-benzyl-5-(4-(methoxymethyl)phenyl)pyrazine-2-amine (30.0 mg, 0.09 mmol, 1 eq.) and 3-(4-((tert-butyldimethylsilyl)oxy)phenyl)-1,1-diethoxypropan-2-one (69.2 mg, 0.19 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 4 hours. After allowing the mixture to cool to room temperature, the mixture was concentrated under reduced pressure, and the residue was purified by silica column chromatography (methylene chloride/methanol=20/1) to obtain 6-Ether-CTZ as a yellow solid (13.8 mg, 31%).

$^{1}$H-NMR (500 MHz, CD$_{3}$OD): δ (ppm)=7.70 (s, 1H), 7.59 (d, J=7.4 Hz, 2H), 7.39-7.18 (m, 7H), 7.14 (d, J=8.3 Hz, 2H), 6.68 (d, J=8.5 Hz, 2H), 4.44 (s, 2H), 4.38 (s, 2H), 4.05 (s, 2H), 3.31-3.30 (m, 3H). $^{13}$C-NMR (150 MHz, CD$_{3}$OD): δ (ppm)=33.22, 35.34, 58.47, 74.94, 108.97, 116.22, 127.80, 128.16, 129.15, 129.27, 129.75, 129.79, 129.89, 130.57, 130.78, 138.05, 141.20, 157.02.

Synthesis Example 17: Synthesis of 6-Ether-2H-CTZ (Comparative Compound)

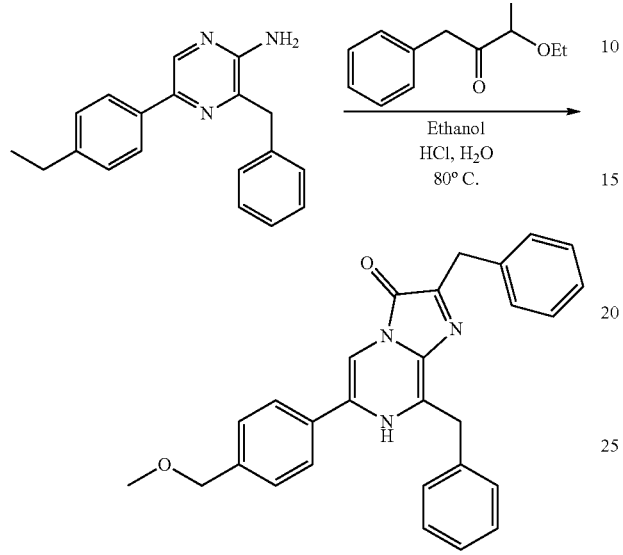

Under an argon atmosphere, 3-benzyl-5-(4-(methoxymethyl)phenyl)pyrazine-2-amine (30.4 mg, 0.09 mmol, 1 eq.) and 1,1-diethoxy-3-phenylpropan-2-one (44.2 mg, 0.19 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 4 hours. After allowing the mixture to cool to room temperature, the mixture was concentrated under reduced pressure, and the residue was purified by silica column chromatography (methylene chloride/methanol=20/1) to obtain 6-Ether-2H-CTZ as a yellow solid (29.35 mg, 68%).

$^1$H-NMR (500 MHz, CD$_3$OD, CDCl$_3$): δ (ppm)=8.32 (s, 1H), 7.83 (d, J=6.0 Hz, 2H), 7.45-7.23 (m, 11H), 4.52 (s, 2H), 4.49 (s, 2H), 4.27 (s, 2H), 3.40 (m, 3H). $^{13}$C-NMR (150 MHz, CD$_3$OD, CDCl$_3$): δ (ppm)=31.67, 37.69, 58.55, 74.86, 110.68, 127.81, 127.84, 128.22, 129.19, 129.41, 129.62, 129.66, 130.01, 133.74, 136.89, 138.30, 141.41, 146.26.

Synthesis Example 18: Synthesis of 6-Methyl-CTZ

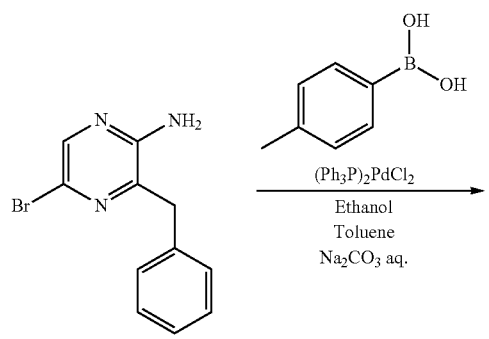

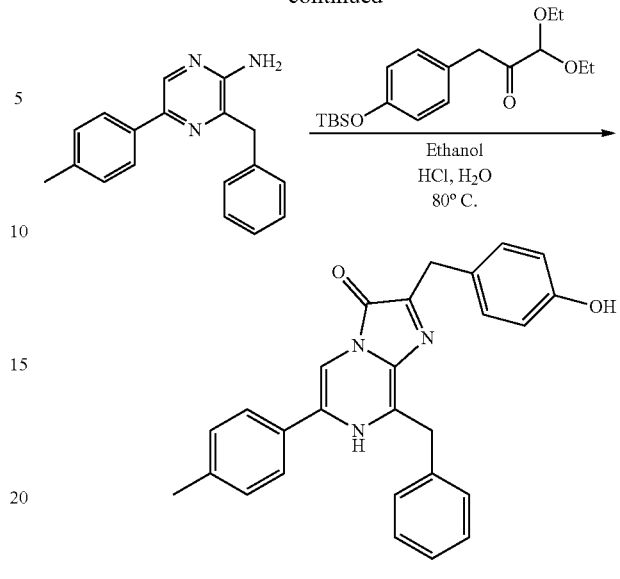

Synthesis Example 18-1

Under a nitrogen atmosphere, 3-benzyl-5-bromopyrazine-2-amine (123.91 mg, 0.4 mmol, 1 eq.) and p-tolylboronic acid (102.02 mg, 0.7 mmol, 1.6 eq.) were dissolved in ethanol (2 ml) and toluene (12 ml). To the solution was added 1 M aqueous sodium carbonate solution (3 ml) and the mixture was stirred at room temperature. The reaction solution was degassed under vacuum. To the solution was added a catalytic amount of tetrakis(triphenylphosphine)palladium (0) (about 1 cup of micro spatula) and the mixture was degassed again under vacuum and then stirred at 100° C. overnight (19 hours). After allowing the mixture to cool to room temperature, the mixture was filtered through Celite to remove palladium catalyst. The resulting residue was extracted with ethyl acetate, washed with distilled water and saturated brine, dried over sodium sulfate, and then concentrated under reduced pressure. The resulting residue was purified by flash column chromatography (eluent: hexane/ethyl acetate=4/1→7/3) to obtain 3-benzyl-5-(p-tolyl)pyrazine-2-amine as a yellow solid (123.97 mg, 96%).

$^1$H-NMR (500 MHz, CDCl$_3$): δ (ppm)=8.38 (s, 1H), 7.82 (d, J=8.0 Hz, 2H), 7.32-7.23 (m, 7H), 4.53 (s, 2H), 4.17 (s, 2H), 2.39 (s, 3H). $^{13}$C-NMR (125 MHz, CDCl$_3$): δ (ppm)= 21.36, 41.34, 125.76, 127.16, 128.68, 129.09, 129.63, 134.50, 136.83, 138.07, 140.92, 142.98, 151.48.

Synthesis Example 18-2

Under an argon atmosphere, 3-benzyl-5-(p-tolyl)pyrazine-2-amine (32.6 mg, 0.11 mmol, 1 eq.) and 3-(4-((tert-butyldimethylsilyl)oxy)phenyl)-1,1-diethoxypropan-2-one (83.68 mg, 0.23 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 21 hours. After allowing the mixture to cool to room temperature, the mixture was concentrated under reduced pressure, and the residue was purified by silica column chromatography (methylene chloride/methanol=20/1→10/1) to obtain 6-Methyl-CTZ as a yellow solid (23.12 mg, 50%).

¹H-NMR (500 MHz, CD₃OD): δ (ppm)=7.57 (s, 1H), 7.42 (d, J=7.4 Hz, 2H), 7.37 (d, J=7.4 Hz, 2H), 7.27-7.13 (m, 7H), 6.68 (d, J=8.3 Hz, 21-1), 4.36 (s, 2H), 4.04 (s, 2H), 2.28 (s, 3H). ¹³C-NMR (125 MHz, CD₃OD): δ (ppm)=21.24, 33.28, 35.13, 108.51, 116.22, 127.62, 127.80, 128.16, 129.74, 129.77, 130.56, 130.62, 130.80, 138.01, 140.89, 157.00.

Synthesis Example 19

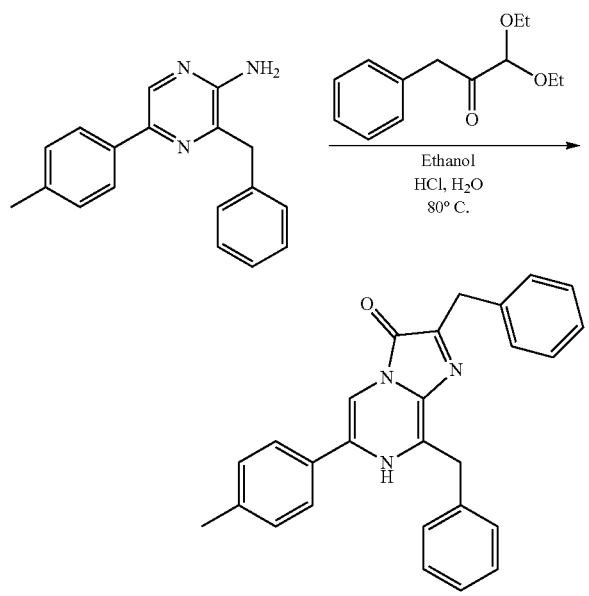

Under an argon atmosphere, 3-benzyl-5-(p-tolyl)pyrazine-2-amine (32.0 mg, 0.11 mmol, 1 eq.) and 1,1-diethoxy-3-phenylpropan-2-one (51.66 mg, 0.23 mmol, 2 eq.) were dissolved in ethanol (2 ml) and milliQ (0.2 ml) and the mixture was cooled to 0° C. The reaction solution was degassed under vacuum, concentrated hydrochloric acid (0.1 ml) was added, and then the mixture was stirred at 80° C. for 4 hours. After allowing the mixture to cool to room temperature, the mixture was concentrated under reduced pressure, and the residue was purified by silica column chromatography (methylene chloride/methanol 40/1→20/1) to obtain 6-Methyl-2H-CTZ as a yellow solid (24.08 mg, 54%).

¹H-NMR (500 MHz, CD₃OD, CDCl₃): δ (ppm)=7.45 (s, 1H), 7.41 (d, J=7.1 Hz, 2H), 7.36 (d, J=7.4 Hz, 2H), 7.31-7.17 (m, 10H), 4.39 (s, 2H), 4.19 (s, 2H), 2.37 (s, 3H). ¹³C-NMR (125 MHz, CD₃OD): δ (ppm)=21.35, 34.03, 34.35, 108.11, 126.94, 127.16, 127.81, 129.02, 129.34, 129.35, 129.58, 130.30, 137.15, 139.08, 140.43.

(44) Method for Measuring Bioluminescence Intensity (*Renilla* Luciferase Luminescence System)

The luciferases were respectively expressed in COST cells using an expression vector (pcDNA3.1(+), commercially available from Invitrogen) comprising the sequence encoding native *Renilla* Luciferase (RLuc) (trade name pGL4.75, commercially available from Promega) or an expression vector (trade name pcDNA3.1(+), commercially available from Invitrogen) comprising the sequence encoding a RLuc derivative RLuc8 or RLuc8.6-535 (Reference: Loening, A. M. et al., Nat. Methods, 2007, 4, 641-643.). The cells were lysed using a *Renilla* Luciferase Lysis Buffer (E291A, Promega), and the lysate was directly used as an enzyme solution. As luminescent substrates, native CTZ (Nanolight technology), 6-Al2OH-CTZ, 6-Al2OH2H-CTZ, 6-Al3OH-CTZ, 6-Al3OH2H-CTZ, 6-Al4OH-CTZ, 6-Al4OH2H-CTZ, 6-Al5OH-CTZ, 6-Al5OH2H-CTZ, 6-Al3OMe-CTZ, 6-Al3OMe2H-CTZ, 6-Alkyl3-CTZ, 6-Alkyl3-2H-CTZ, 6-Methoxy-CTZ, 6-Methoxy-2H-CTZ, 6-Ethyl-CTZ, 6-Ethyl-2H-CTZ, 6-Methyl-CTZ, CTZ, 6-Ether-CTZ (comparative compound), and 6-Ether-2H-CTZ (comparative compound), as well as an existing blue-shifted derivative DeepBlueC (trade name, Nanolight technology) for comparison, were used. Bioluminescence was measured according to the protocol of *Renilla* Luciferase Assay System (Cat. No. E 2810; Promega). The luminescent substrate was dissolved in methanol to prepare a 2 mM solution. The solution was diluted to 2 μM with PBS buffer (pH 7.4), and the diluted solution was used as a substrate solution. To 200 μL of the substrate solution, 4 μL of the cell lysate containing RLuc, RLuc 8 or RLuc8.6-535 was added to start the luminescent reaction. The luminescence intensity was measured with a Berthold Lumat LB 9507 for 1 second, and indicated by the maximum luminescence intensity (I). The luminescence intensity of the native CTZ by RLuc8 was set to be 1.0, and the other bioluminescence intensities were normalized to be relative values to that of native CTZ. The results are shown in FIG. 1 and Table 2 below.

TABLE 2

Comparison of bioluminescence intensity

| Example | | RLuc luminescence intensity (%) | RLuc8 luminescence intensity (%) | RLuc8.6-535 luminescence intensity (%) |
|---|---|---|---|---|
| Comparative Example 1 | Native-CTZ | 10.7 | 80.5 | 100 |
| Example 1 | 6-Alkyl2OH-CTZ | N.D. | 15.0 | 43.2 |
| Example 2 | 6-Alkyl2OH-2H-CTZ | N.D. | 6.21 | 6.24 |
| Example 3 | 6-Alkyl3OH-CTZ | 0.11 | 9.74 | 75.3 |
| Example 4 | 6-Alkyl3OH-2H-CTZ | N.D. | 5.03 | 23.9 |
| Example 5 | 6-Alkyl4OH-CTZ | N.D. | 11.8 | 59.8 |
| Example 6 | 6-Alkyl4OH-2H-CTZ | N.D. | 3.45 | 23.9 |
| Example 7 | 6-Alkyl5OH-CTZ | N.D. | 3.75 | 22.5 |
| Example 8 | 6-Alkyl5OH-2H-CTZ | N.D. | 2.88 | 18.0 |
| Example 9 | 6-Alkyl3OMe-CTZ | N.D. | 9.19 | 41.1 |
| Example 10 | 6-Alkyl3OMe-2H-CTZ | N.D. | 2.93 | 29.3 |
| Example 11 | 6-Alkyl3-CTZ | N.D. | 8.07 | 39.6 |
| Example 12 | 6-Alkyl3-2H-CTZ | N.D. | 2.00 | 28.4 |
| Example 13 | 6-Ethyl-CTZ | N.D. | 2.68 | 29.4 |
| Example 14 | 6-Ethyl-2H-CTZ | N.D. | 0.62 | 18.0 |
| Example 15 | 6-Methyl-CTZ | N.D. | 2.72 | 41.0 |
| Example 16 | 6-Methyl-2H-CTZ | N.D. | 1.44 | 25.3 |
| Comparative Example 2 | 6-Ether-CTZ | N.D. | 0.85 | 8.94 |
| Comparative Example 3 | 6-Ether-2H-CTZ | N.D. | 0.36 | 2.17 |
| Comparative Example 4 | DeepBlueC (trade name) | N.D. | 2.30 | 5.80 |

N.D.: not detected due to low luminescence intensity (the same shall apply hereinafter)

As shown in FIG. 1 and Table 1, the novel compounds of the present invention were recognized by the enzymes RLuc8 and RLuc8.6-535 and emitted significant luminescence. In particular, the combination of 6-Alkyl3OH-CTZ/RLuc8.6-535 was found to show 32-fold higher luminescence intensity than that of the conventional blue-shifted RLuc luminescence system (DeepBlueC (trade name)/RLuc8).

(45) Method for Measuring Bioluminescence Spectrum (*Renilla* Luciferase Luminescence System)

As in the method for measuring bioluminescence intensity described above, luminescence spectrum was measured according to the protocol of *Renilla* Luciferase Assay System (Cat. No. E 2810; Promega). The luminescence spectrum was measured using ATTO LumiFL. The maximum luminescence intensities were normalized to be relative values to 1.0 upon determination of the maximum luminescence wavelength.

TABLE 3

Comparison of bioluminescence wavelength with RLuc 8 or RLuc 8.6

|  | RLuc8 maximum luminescence wavelength (nm) [half-width (nm)] | RLuc8.6-535 maximum luminescence wavelength (nm) [half-width (nm)] |
| --- | --- | --- |
| Native-CTZ | 484 [98] | 538 [111] |
| 6-Alkyl2OH-CTZ | 411 [59] | 411 [56] |
| 6-Alkyl2OH-2H-CTZ | 413 [65] | 407 [68] |
| 6-Alkyl3OH-CTZ | 414 [60] | 415 [56] |
| 6-Alkyl3OH-2H-CTZ | 411 [65] | 413 [56] |
| 6-Alkyl4OH-CTZ | 404 [69] | 412 [60] |
| 6-Alkyl4OH-2H-CTZ | 404 [69] | 405 [68] |
| 6-Alkyl5OH-CTZ | 403 [70] | 406 [66] |
| 6-Alkyl5OH-2H-CTZ | 403 [70] | 406 [68] |
| 6-Alkyl3OMe-CTZ | (418) [44] | 412 [59] |
| 6-Alkyl3OMe-2H-CTZ | 416 [49] | 413 [53] |
| 6-Alkyl3-CTZ | (413) [46] | 412 [60] |
| 6-Alkyl3-2H-CTZ | 411 [50] | 413 [53] |
| 6-Ethyl-CTZ | (410) [—] | 406 [60] |
| 6-Ethyl-2H-CTZ | (402) [—] | 411 [50] |
| 6-Methyl-CTZ | 415 [44] | 413 [51] |
| 6-Methyl-2H-CTZ | 408 [45] | 411 [49] |
| 6-Ether-CTZ | (420) [—] | 411 [49] |
| 6-Ether-2H-CTZ | (393) [—] | 406 [53] |
| DeepBlueC ™ | 416 [57] | 410 [51] |

The 6-Alkyl3OH-CTZ/RLuc8.6-535 luminescence system which showed high-intensity luminescence in the above heading (44) was found to show almost the same bioluminescence wavelength (415 nm) as that of the conventional blue-shifted RLuc luminescence system (DeepBlueC (trade name)/RLuc8). Thus, it can be said that we succeeded in developing a blue-shifted RLuc luminescence system with the world's highest luminescence intensity.

(46) Method for Measuring Bioluminescence Intensity (Artificial Bioluminescent Enzyme ALuc System)

Figure 3:
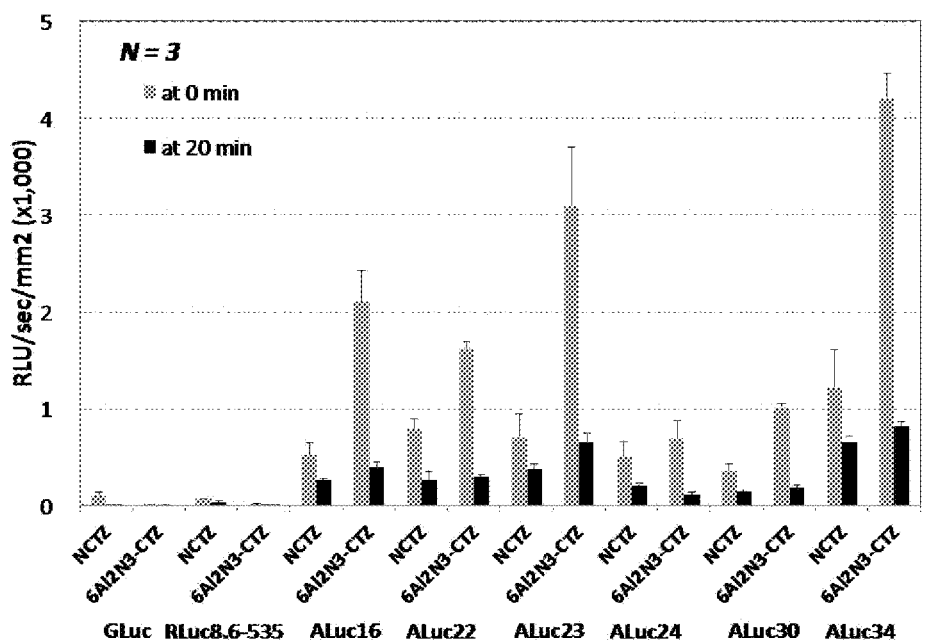
FIG. 3 shows the luminescence intensities of 6-Al2N3-CTZ, a compound obtained in Example of the present invention, and Native CTZ, a known coelenteramine derivative, in various luciferase luminescence systems.

The luciferases were expressed in COST cells using an expression vector (pcDNA3.1(+), commercially available from Invitrogen) comprising the sequence encoding GLuc, RLuc8.6-535 or Artificial bioluminescent enzyme (ALuc) selected from the luciferase family consisting of ALuc16, ALuc22, ALuc23, and ALuc34 (see Kim S. B. et al., Bioconjugate Chem., 2013, 24, 2067-2075., Kim S. B. et al., Biochem. Biophys. Res. Commun., 2014, 448, 418-423., Kim S. B. et al., Anal. Sci., 2015, 31, 1-6., Kim S. B. et al., Bioconjugate Chem., 27, 354-362.). The cells were lysed using a *Renilla* Luciferase Buffer (E291A; Promega), and the lysate was directly used as an enzyme solution. As luminescent substrates, native CTZ (Nanolight technology) and 6-Al2N3-CTZ (Example 17) were used. Bioluminescence was measured according to the protocol of a *Renilla* Luciferase Assay System (Cat. No. E2810; Promega). The luminescent substrate was dissolved in methanol to prepare a 1 mM solution. The solution was diluted to 1 μM with Promega buffer, and the diluted solution was used as a substrate solution. To 40 μL of the substrate solution, 10 μL of the cell lysate containing RLuc8.6-535, ALuc16, ALuc22, ALuc23 or ALuc34 was added for starting the luminescent reaction. Using Fujifilm LAS-4000, the luminescence intensities were measured 0 and 20 minutes after the start of the enzyme reaction. The results are shown in FIG. 3. Further, from the results of bioluminescence intensity shown in FIG. 3, the bioluminescence intensities were summarized in Tables 4-1 and 4-2 below, where the luminescence intensities were normalized to be the relative values of nCTZ/ALuc34 (100%).

TABLE 4-1

Comparison of bioluminescence intensity (0 minutes after the start of measurement)

|  | nCTZ luminescence intensity (%) | 6Al2N3-CTZ luminescence intensity (%) |
| --- | --- | --- |
| GLuc | 0.08 | N.D. |
| RLuc8.6-535 | 0.05 | 0.01 |
| ALuc16 | 0.43 | 1.72 |
| ALuc22 | 0.65 | 1.32 |
| ALuc23 | 0.58 | 2.53 |
| ALuc24 | 0.40 | 0.56 |
| ALuc30 | 0.28 | 0.83 |
| ALuc34 | 1.0 | 3.45 |

TABLE 4-2

Comparison of bioluminescence intensity (20 minutes after the start of measurement)

| | nCTZ luminescence intensity (%) | 6Al2N3-CTZ luminescence intensity (%) |
|---|---|---|
| GLuc | ND. | N.D. |
| RLuc8.6-535 | 0.05 | N.D. |
| ALuc16 | 0.42 | 0.60 |
| ALuc22 | 0.42 | 0.46 |
| ALuc23 | 0.58 | 1.00 |
| ALuc24 | 0.31 | 0.17 |
| ALuc30 | 0.21 | 0.28 |
| ALuc34 | 1 | 1.27 |

The combination of artificial bioluminescent enzyme (ALuc) and native CTZ exerts an ultra-high luminance bioluminescence system that exhibits about 50 fold higher luminescence intensity in the same wavelength range (480-500 nm) than that of the conventional RLuc luminescence system and will enable high-sensitivity bioassays using ALuc. FIG. 3 shows the bioluminescence intensities of the newly-developed 6-Alkyl2N3-CTZ and native CTZ with GLuc, RLuc8.6-535, or ALuc group (ALuc16, ALuc22, ALuc23, ALuc24, ALuc30, or ALuc34). From FIG. 3 and Table 4, it was found that the novel derivative 6-Alkyl2N3-CTZ/ALuc34 luminescence system showed luminescence intensity about 3.4 fold higher than that of native CTZ/ALuc34 immediately after the start of the measurement.

(47) Method for Measuring Bioluminescence Spectrum (Artificial Bioluminescent Enzyme ALuc System)

Figure 4:
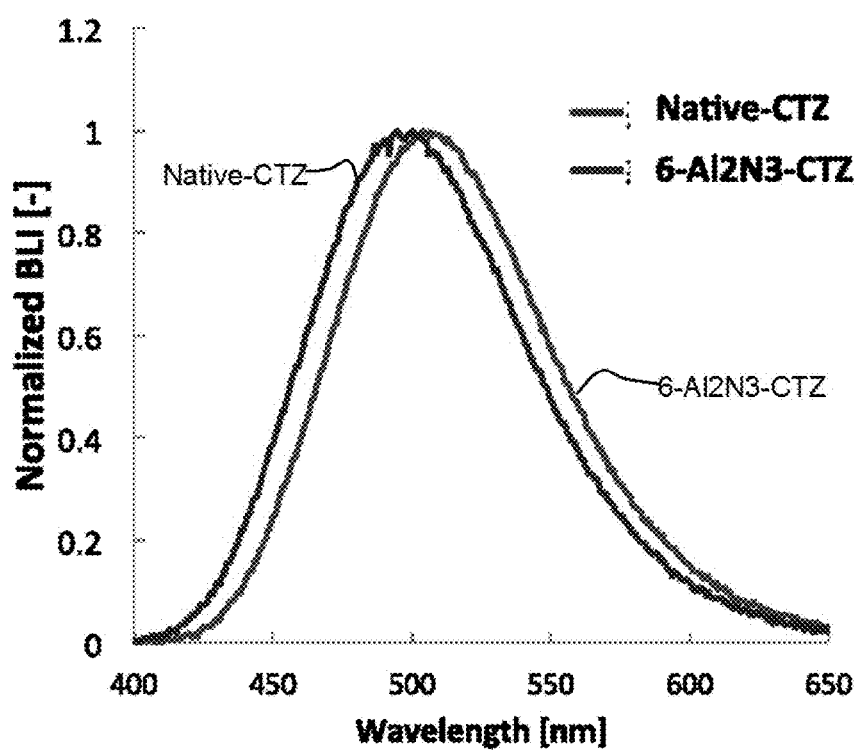
FIG. 4 shows the luminescence wavelengths of 6-Al2N3-CTZ, a compound obtained in Example of the present invention, and Native CTZ, a known coelenteramine derivative, with ALuc34.

As in the method for measuring bioluminescence intensity described above, the corresponding luminescence spectra were measured according to the protocol of a *Renilla* Luciferase Assay System (Cat. No. E2810; Promega). The luminescence spectrum was measured using ATTO LumiFL. The maximum luminescence intensity was normalized to 1.0 upon determination of the maximum luminescence wavelength. The results are shown in Table 5 below and FIG. 4.

TABLE 5

Comparison of bioluminescence wavelength with ALuc34

| | NCTZ | 6-Al2N3-CTZ |
|---|---|---|
| ALuc34 maximum luminescence intensity (nm) [half-width] | 500 [90] | 503 [90] |

6-Alkyl2N3-CTZ (compound of the present invention obtained in Example 17)/ALuc34 luminescence system was found to show almost the same luminescence wavelength as that of native CTZ/ALuc34. Thus, it can be said that we succeeded in constructing a novel RLuc luminescence system with high luminescence intensity.

The design of the CTZ derivatives obtained in the present invention can also be applied to other bioluminescence systems. For example, *Oplophorus gracilirostris* utilizes CTZ as luminescent substrate. Recently, NanoLuc (trade name) (Promega), a Luciferase derived from *Oplophorus gracilirostris* (see Hall P. M. et al., ACS. Chem. Biol., 2012, 7, 1848-1857.) was developed and combined with a novel substrate Furimazine (the following Formula [III]) to construct a novel bioluminescence system which shows luminescence intensity about 100 fold higher than that of the firefly luciferase luminescence system. NanoLuc (trade name) (Promega) also enables bioassays with high S/N ratio due to its high luminescence intensity. In fact, application of NanoLuc not only to reporter assays but also to various bioassay systems including protein-protein interaction analysis utilizing bioluminescence resonance energy transfer (BRET) mechanism has been demonstrated (see England G C et al., Bioconjugate Chem., 2016, 27, 1175-1187.).

Studies on basal substrate synthesis for NanoLuc (trade name) (Promega) have reported, where the derivatives were modified at the 6- and 2-positions of CTZ (see Hall P. M. et al., ACS. Chem. Biol., 2012, 7, 1848-1857., and Shakhmin A. et al., Chem. Eur. J., 2016, 22, 10369-10375.). In both references, the influence of the 2-position substituent on the enzyme activity has been intensively investigated. According to the present invention, the influence of modification of the 6-position substituent of CTZ on the enzyme activity is great, so that NanoLuc (trade name) (Promega) with further higher luminescence intensity can be expected by developing a novel substrate obtained by modification of 6-position of CTZ.

The luminescent enzyme *Oplophorus* Luciferase (OLase) of *Oplophorus gracilirostris* has its function of catalyzing luminescence in a protein domain with a molecular weight of 19 kDa and thus is said 19kOLase. NanoLuc (trade name) (Promega) and nanoKAZ (see Inouye S. et al., Biochem. Biophys. Res. Commun., 2013, 437, 23-28.) are known as variants of 19kOLase. Based on the results of structure-activity correlation studies between these 19kOLase, nanoKAZ, NanoLuc™ (Promega) and known CTZ derivatives, novel substrates (the following Formula [IV] and Formula [V]) are proposed below.

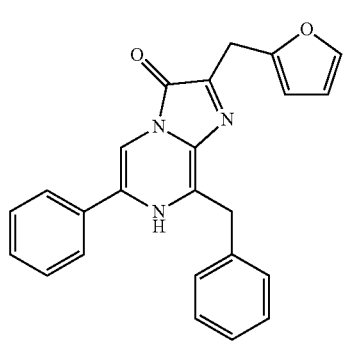

Formula [III]

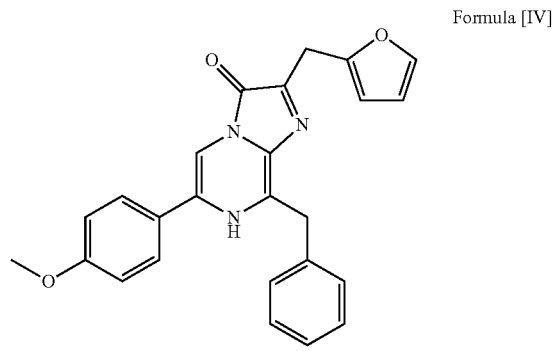

Formula [IV]

Formula [V]

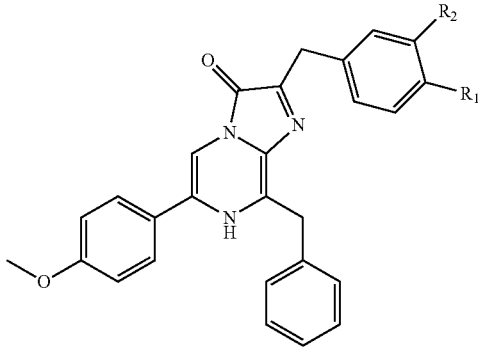

In the Formula [V], $R^1$ and $R^2$ are as shown in the Table 6 below.

TABLE 6

| $R^1$ | $R^2$ |
| --- | --- |
| —F | —H |
| —H | —O—CH$_3$ |
| —H | —CH$_3$ |

The invention claimed is:

1. A compound represented by Formula [II]:

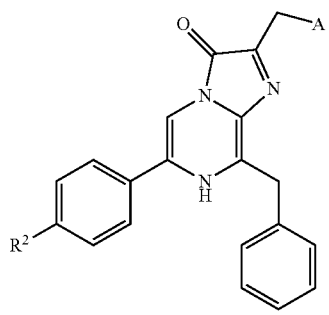

[II]

wherein,

A represents

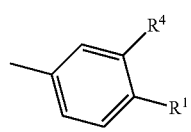

wherein, $R^1$ represents hydrogen, hydroxy or fluorine; and $R^4$ represents hydrogen, methyl or methoxy; or A represents

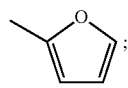

and
$R^2$ represents (1) —O—(CH$_2$)$_n$—R$^3$, where n is an integer from 1 to 5; and R$^3$ represents hydroxy, methoxy, methyl or azido; or (2) C$_1$- or C$_2$-alkyl.

2. A compound represented by Formula [I]:

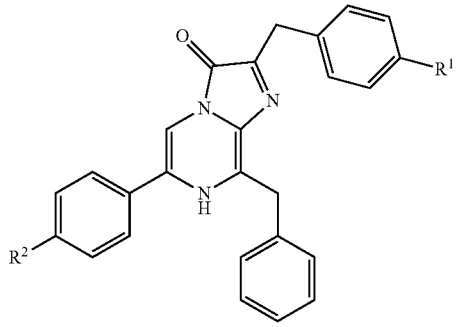

[I]

wherein,
$R^1$ represents hydrogen or hydroxy; and
$R^2$ represents (1) —O—(CH$_2$)$_n$—R$^3$, where n is an integer from 2 to 5; and R$^3$ represents hydroxy, methoxy, methyl or azido; or (2) C$_1$- or C$_2$-alkyl.

3. The compound according to claim 2, wherein said $R^1$ and $R^2$ each represent a group or an atom shown in Table 1 below:

TABLE 1

| $R^1$ | $R^2$ |
| --- | --- |
| —OH | —O—(CH$_2$)$_2$—OH |
| —OH | —O—(CH$_2$)$_3$—OH |
| —OH | —O—(CH$_2$)$_4$—OH |
| —OH | —O—(CH$_2$)$_5$—OH |
| —OH | —O—(CH$_2$)$_3$—OCH$_3$ |
| —OH | —O—(CH$_2$)$_2$—N$_3$ |
| —OH | —O—(CH$_2$)$_3$—CH$_3$ |
| —H | —O—(CH$_2$)$_2$—OH |
| —H | —O—(CH$_2$)$_3$—OH |
| —H | —O—(CH$_2$)$_4$—OH |
| —H | —O—(CH$_2$)$_5$—OH |
| —H | —O—(CH$_2$)$_3$—OCH$_3$ |
| —H | —O—(CH$_2$)$_3$—CH$_3$ |
| —OH | —C$_2$H$_5$ |
| —H | —C$_2$H$_5$ |
| —OH | —CH$_3$ |
| —H | —CH$_3$. |

4. The compound according to claim 3, wherein $R^1$ represents —OH, and $R^2$ represents —O—(CH$_2$)$_3$—OH.

5. The compound according to claim 3, wherein $R^1$ represents —OH, and $R^2$ represents —O—(CH$_2$)$_2$—N$_3$.

6. A method of generating luminescence, comprising contacting the compound according to any one of claims 1 to 5 with a luciferase.

* * * * *